US012582622B2

(12) United States Patent
Skobieranda et al.

(10) Patent No.: US 12,582,622 B2
(45) **Date of Patent: *Mar. 24, 2026**

(54) SODIUM OXYBATE TO TREAT IDIOPATHIC HYPERSOMNIA

(71) Applicant: Jazz Pharmaceuticals Ireland Limited, Dublin (IE)

(72) Inventors: Franck Skobieranda, Palo Alto, CA (US); Dan Chen, Palo Alto, CA (US); Amanda Leigh Sterkel, Palo Alto, CA (US)

(73) Assignee: JAZZ PHARMACEUTICALS IRELAND LIMITED, Dublin (IE)

( * ) Notice: Subject to any disclaimer, the term of this patent is extended or adjusted under 35 U.S.C. 154(b) by 465 days.

This patent is subject to a terminal disclaimer.

(21) Appl. No.: 18/248,499

(22) PCT Filed: Oct. 8, 2021

(86) PCT No.: PCT/US2021/054179

§ 371 (c)(1),
(2) Date: Apr. 10, 2023

(87) PCT Pub. No.: WO2022/076824

PCT Pub. Date: Apr. 14, 2022

(65) Prior Publication Data

US 2023/0404950 A1 Dec. 21, 2023

Related U.S. Application Data

(60) Provisional application No. 63/089,428, filed on Oct. 8, 2020.

(51) Int. Cl.
*A61K 31/19* (2006.01)
*A61P 25/20* (2006.01)

(52) U.S. Cl.
CPC .............. *A61K 31/19* (2013.01); *A61P 25/20* (2018.01)

(58) Field of Classification Search
CPC ........... A61K 31/19; A61P 25/20; A61P 25/00
See application file for complete search history.

(56) References Cited

U.S. PATENT DOCUMENTS 3,051,619 A 8/1962 Marie et al.
3,419,588 A 12/1968 De et al.
4,221,778 A 9/1980 Raghunathan
4,374,441 A 2/1983 Carter et al.
4,393,236 A 7/1983 Klosa
4,510,128 A 4/1985 Khanna
4,524,217 A 6/1985 Davenport et al.
4,684,516 A 8/1987 Bhutani
4,687,662 A 8/1987 Schobel
4,738,985 A 4/1988 Kluger et al.
4,916,161 A 4/1990 Patell
4,939,949 A 7/1990 Langenberg
4,983,632 A 1/1991 Gessa et al.
5,294,430 A 3/1994 Borch et al.
5,380,937 A 1/1995 Koehler et al.
5,415,870 A 5/1995 Gergely et al.
5,594,030 A 1/1997 Conte et al.
5,753,708 A 5/1998 Koehler et al.
5,758,095 A 5/1998 Albaum et al.
5,833,599 A 11/1998 Schrier et al.
5,840,331 A 11/1998 Van Cauter et al.
5,845,255 A 12/1998 Mayaud
5,858,998 A 1/1999 Leuschner
5,955,106 A 9/1999 Moeckel et al.
5,990,162 A 11/1999 Scharf
6,014,631 A 1/2000 Teagarden et al.
6,022,562 A 2/2000 Autant et al.
6,067,524 A 5/2000 Byerly et al.
6,103,292 A 8/2000 Del Vecchio
6,112,182 A 8/2000 Akers et al.
6,317,719 B1 11/2001 Schrier et al.
6,322,819 B1 11/2001 Burnside et al.
6,356,873 B1 3/2002 Teagarden et al.
6,384,020 B1 5/2002 Flanner et al.
6,436,998 B1 8/2002 Cacciaglia et al.
6,472,431 B2 10/2002 Cook et al.
6,472,432 B1 10/2002 Perricone
6,495,598 B1 12/2002 Yoneda et al.
6,565,872 B2 5/2003 Wu et al.
6,780,889 B2 8/2004 Cook et al.
7,015,200 B2 3/2006 Mamelak et al.
7,072,840 B1 7/2006 Mayaud
7,262,219 B2 8/2007 Cook et al.
7,568,822 B2 8/2009 Ibrahim
7,668,730 B2 2/2010 Reardan et al.
7,765,106 B2 7/2010 Reardan et al.
(Continued)

FOREIGN PATENT DOCUMENTS

AU 2011224350 A1 10/2012
CA 2112663 C 4/2002
(Continued)

OTHER PUBLICATIONS

21 C.F.R. 184, Food and Drug Administration, HHS, (1998), pp. 441-535.
Activase, Physicians Desk Reference (50th ed.), (1996), pp. 312, 1058-1061.
Ahmed et al., "Overview of Central Disorders of Hypersomnolence," Reference Module in Neuroscience and Biobehavioral Psychology, 2017, 7 pages.
Akifuddin et al. "Preparation, characterization and in-vitro evaluation of microcapsules for controlled release of Diltiazem hydrochloride by Ionotropic gelation technique." Journal of Applied Pharmaceutical Science (2013); 3.4: 35-42.
(Continued)

*Primary Examiner* — Kevin E Weddington
(74) *Attorney, Agent, or Firm* — COOLEY LLP

(57) ABSTRACT

The present disclosure relates to methods of treating idiopathic hypersomnia with oxybate, preferably sodium oxybate.

29 Claims, 6 Drawing Sheets

(56) References Cited

U.S. PATENT DOCUMENTS

| | | | |
|---|---|---|---|
| 7,765,107 | B2 | 7/2010 | Reardan et al. |
| 7,797,171 | B2 | 9/2010 | Reardan et al. |
| 7,851,506 | B2 | 12/2010 | Cook et al. |
| 7,895,059 | B2 | 2/2011 | Reardan et al. |
| 8,101,209 | B2 | 1/2012 | Legrand et al. |
| 8,193,211 | B2 | 6/2012 | Liang et al. |
| 8,202,537 | B2 | 6/2012 | Mehta et al. |
| 8,263,125 | B2 | 9/2012 | Vaya et al. |
| 8,263,650 | B2 | 9/2012 | Cook et al. |
| 8,324,275 | B2 | 12/2012 | Cook et al. |
| 8,457,988 | B1 | 6/2013 | Reardan et al. |
| 8,461,197 | B2 | 6/2013 | Tung |
| 8,461,203 | B2 | 6/2013 | Cook et al. |
| 8,529,954 | B2 | 9/2013 | Lebon et al. |
| 8,589,182 | B1 | 11/2013 | Reardan et al. |
| 8,591,922 | B1 | 11/2013 | Allphin et al. |
| 8,598,191 | B2 | 12/2013 | Liang et al. |
| 8,680,228 | B2 | 3/2014 | Guo et al. |
| 8,731,963 | B1 | 5/2014 | Reardan et al. |
| 8,759,394 | B2 | 6/2014 | Tung et al. |
| 8,771,735 | B2 | 7/2014 | Rourke et al. |
| 8,772,306 | B1 | 7/2014 | Eller |
| 8,778,301 | B2 | 7/2014 | Mamelak et al. |
| 8,778,398 | B2 | 7/2014 | Rourke et al. |
| 8,859,619 | B2 | 10/2014 | Cook et al. |
| 8,901,173 | B2 | 12/2014 | Allphin et al. |
| 8,952,029 | B2 | 2/2015 | Eller |
| 8,952,062 | B2 | 2/2015 | Cook et al. |
| 9,023,400 | B2 | 5/2015 | Guimberteau et al. |
| 9,050,302 | B2 | 6/2015 | Eller |
| 9,132,107 | B2 | 9/2015 | Allphin et al. |
| 9,486,426 | B2 | 11/2016 | Eller |
| 9,539,330 | B2 | 1/2017 | Cook et al. |
| 9,555,017 | B2 | 1/2017 | Allphin et al. |
| 9,770,514 | B2 | 9/2017 | Ghebre-Sellassie et al. |
| 9,795,567 | B2 | 10/2017 | Rourke et al. |
| 9,801,852 | B2 | 10/2017 | Allphin |
| 10,195,168 | B2 | 2/2019 | Allphin et al. |
| 10,213,400 | B2 | 2/2019 | Eller |
| 10,272,062 | B2 | 4/2019 | Megret et al. |
| 10,398,662 | B1 | 9/2019 | Allphin et al. |
| 10,675,258 | B2 | 6/2020 | Allphin et al. |
| 10,736,866 | B2 | 8/2020 | Megret et al. |
| 10,758,488 | B2 | 9/2020 | Allphin et al. |
| 10,813,885 | B1 | 10/2020 | Allphin et al. |
| 10,925,844 | B2 | 2/2021 | Grassot et al. |
| 10,952,986 | B2 | 3/2021 | Megret et al. |
| 10,959,956 | B2 | 3/2021 | Allphin et al. |
| 10,966,931 | B2 | 4/2021 | Allphin et al. |
| 10,973,795 | B2 | 4/2021 | Megret et al. |
| 10,987,310 | B2 | 4/2021 | Allphin et al. |
| 11,065,224 | B2 | 7/2021 | Megret et al. |
| 11,077,079 | B1 | 8/2021 | Allphin |
| 11,090,269 | B1 | 8/2021 | Allphin et al. |
| 11,147,782 | B1 | 10/2021 | Allphin et al. |
| 11,207,270 | B2 | 12/2021 | Allphin et al. |
| 11,364,215 | B1 | 6/2022 | Allphin et al. |
| 11,400,052 | B2 | 8/2022 | Walsh et al. |
| 11,426,373 | B2 | 8/2022 | Allphin et al. |
| 12,138,233 | B2 * | 11/2024 | Skobieranda .......... A61K 31/19 |
| 12,167,991 | B2 | 12/2024 | Grassot et al. |
| 12,167,992 | B2 | 12/2024 | Grassot et al. |
| 12,186,298 | B2 | 1/2025 | Dubow |
| 12,226,389 | B2 | 2/2025 | Mégret et al. |
| 12,239,625 | B2 | 3/2025 | Mégret et al. |
| 12,257,223 | B2 | 3/2025 | Mégret et al. |
| 12,263,150 | B2 | 4/2025 | Mégret et al. |
| 12,263,151 | B2 | 4/2025 | Mégret et al. |
| 12,303,478 | B2 | 5/2025 | Grassot et al. |
| 2002/0077334 | A1 | 6/2002 | Cook et al. |
| 2003/0180249 | A1 | 9/2003 | Khanna et al. |
| 2004/0092455 | A1 | 5/2004 | Mamelak et al. |
| 2004/0132633 | A1 | 7/2004 | Carter et al. |
| 2004/0224076 | A1 | 11/2004 | Derrien et al. |
| 2005/0031688 | A1 | 2/2005 | Ayala |
| 2005/0037077 | A1 | 2/2005 | Legrand et al. |
| 2005/0113366 | A1 | 5/2005 | Bourguignon et al. |
| 2005/0142192 | A1 | 6/2005 | Benjamin et al. |
| 2006/0018933 | A1 | 1/2006 | Vaya et al. |
| 2006/0024365 | A1 | 2/2006 | Vaya et al. |
| 2006/0069040 | A1 | 3/2006 | Mamelak |
| 2006/0078614 | A1 | 4/2006 | Venkatesh |
| 2006/0210630 | A1 | 9/2006 | Liang et al. |
| 2006/0228410 | A1 | 10/2006 | Dumont et al. |
| 2007/0270491 | A1 | 11/2007 | Cook et al. |
| 2008/0003267 | A1 | 1/2008 | Spencer et al. |
| 2008/0069871 | A1 | 3/2008 | Vaughn et al. |
| 2008/0085304 | A1 | 4/2008 | Baichwal et al. |
| 2008/0118571 | A1 | 5/2008 | Lee et al. |
| 2008/0226564 | A1 | 9/2008 | Weers et al. |
| 2008/0292700 | A1 | 11/2008 | Nghiem et al. |
| 2008/0293698 | A1 | 11/2008 | Johnson |
| 2009/0137565 | A1 | 5/2009 | Frucht |
| 2009/0155357 | A1 | 6/2009 | Muhuri |
| 2009/0317355 | A1 | 12/2009 | Roth et al. |
| 2010/0055133 | A1 | 3/2010 | Duffield et al. |
| 2010/0112056 | A1 | 5/2010 | Rourke et al. |
| 2010/0266701 | A1 | 10/2010 | Guimberteau et al. |
| 2011/0034727 | A1 | 2/2011 | Luchi et al. |
| 2011/0039929 | A1 | 2/2011 | Cook et al. |
| 2011/0054038 | A1 | 3/2011 | Glozman |
| 2011/0091537 | A1 | 4/2011 | Castan et al. |
| 2011/0111027 | A1 | 5/2011 | Rourke et al. |
| 2011/0213004 | A1 | 9/2011 | Kim et al. |
| 2012/0020833 | A1 | 1/2012 | Cook et al. |
| 2012/0076865 | A1 | 3/2012 | Allphin et al. |
| 2012/0148672 | A1 | 6/2012 | Mehta et al. |
| 2012/0202879 | A1 | 8/2012 | Cook et al. |
| 2012/0202880 | A1 | 8/2012 | Cook et al. |
| 2013/0230587 | A1 | 9/2013 | Pilgaonkar et al. |
| 2013/0273159 | A1 | 10/2013 | Howard et al. |
| 2014/0004202 | A1 | 1/2014 | Suplie et al. |
| 2014/0037745 | A1 | 2/2014 | Liang et al. |
| 2014/0072624 | A1 | 3/2014 | Jung et al. |
| 2014/0093578 | A1 | 4/2014 | Mehta et al. |
| 2014/0127306 | A1 | 5/2014 | Mehta et al. |
| 2014/0141090 | A1 | 5/2014 | Wilson |
| 2014/0171506 | A1 | 6/2014 | Allphin et al. |
| 2014/0271896 | A1 | 9/2014 | Abu Shmeis et al. |
| 2014/0275244 | A1 | 9/2014 | Khayrallah et al. |
| 2014/0348917 | A1 | 11/2014 | Rourke et al. |
| 2015/0005334 | A1 | 1/2015 | Shah et al. |
| 2015/0073052 | A1 | 3/2015 | Cook et al. |
| 2015/0328168 | A1 | 11/2015 | Daviaud-Venet et al. |
| 2016/0068463 | A1 | 3/2016 | Peoples et al. |
| 2016/0228379 | A1 | 8/2016 | Kumar et al. |
| 2016/0271070 | A1 | 9/2016 | Singh et al. |
| 2016/0338966 | A1 | 11/2016 | Guimberteau et al. |
| 2016/0346200 | A1 | 12/2016 | Sommer et al. |
| 2016/0346216 | A1 | 12/2016 | Chen |
| 2017/0119627 | A1 | 5/2017 | Bhargava et al. |
| 2017/0340519 | A9 | 11/2017 | Bhargava et al. |
| 2018/0008539 | A1 | 1/2018 | Singh et al. |
| 2018/0021284 | A1 | 1/2018 | Megret et al. |
| 2018/0042855 | A1 | 2/2018 | Rourke et al. |
| 2018/0263936 | A1 | 9/2018 | Allphin et al. |
| 2018/0318222 | A1 | 11/2018 | Allphin et al. |
| 2019/0183806 | A1 | 6/2019 | Guillard |
| 2019/0183836 | A1 | 6/2019 | Mégret et al. |
| 2019/0269640 | A1 | 9/2019 | Megret et al. |
| 2019/0269641 | A1 | 9/2019 | Megret et al. |
| 2019/0274990 | A1 | 9/2019 | Megret et al. |
| 2019/0282532 | A1 | 9/2019 | Megret et al. |
| 2020/0113840 | A1 | 4/2020 | Allphin et al. |
| 2020/0197347 | A1 | 6/2020 | Megret et al. |
| 2020/0276142 | A1 | 9/2020 | Grassot et al. |
| 2020/0330393 | A1 | 10/2020 | Walsh et al. |
| 2020/0360293 | A1 | 11/2020 | Guillard |
| 2020/0360319 | A1 | 11/2020 | Grassot et al. |
| 2020/0368187 | A1 | 11/2020 | Grassot et al. |
| 2021/0093575 | A1 | 4/2021 | Rourke et al. |
| 2021/0121423 | A1 | 4/2021 | Allphin et al. |
| 2021/0186907 | A1 | 6/2021 | Skobieranda |
| 2021/0361601 | A1 | 11/2021 | Skobieranda |

(56) References Cited

U.S. PATENT DOCUMENTS

2022/0008367 A1 1/2022 Skobieranda et al.
2022/0096384 A1 3/2022 Allphin et al.
2022/0160640 A1 5/2022 Walsh et al.
2023/0390228 A1 12/2023 Skobieranda et al.
2024/0285560 A1 8/2024 Skobieranda
2024/0350437 A1 10/2024 Grassot et al.
2024/0350438 A1 10/2024 Grassot et al.
2024/0358666 A1 10/2024 Dubow
2024/0358667 A1 10/2024 Mégret et al.
2024/0366547 A1 11/2024 Mégret et al.
2024/0366548 A1 11/2024 Mégret et al.
2024/0398733 A1 12/2024 Skobieranda
2025/0009704 A1 1/2025 Mégret et al.
2025/0009705 A1 1/2025 Mégret et al.
2025/0017882 A1 1/2025 Grassot et al.
2025/0025437 A1 1/2025 Mégret et al.
2025/0073192 A1 3/2025 Skobieranda et al.
2025/0099417 A1 3/2025 Mégret et al.
2025/0144057 A1 5/2025 Grassot et al.
2025/0152546 A1 5/2025 Vaughn et al.

FOREIGN PATENT DOCUMENTS

CA 2510289 A1 7/2004
CN 102905688 A 1/2013
CN 102958930 A 3/2013
CN 103209966 A 7/2013
CN 103209967 A 7/2013
EP 0203768 A2 12/1986
EP 0235408 A1 9/1987
EP 0344704 A1 12/1989
EP 0616804 A1 9/1994
EP 0635265 A1 1/1995
EP 0709087 B1 12/1999
EP 0635265 B1 2/2000
EP 1140061 A2 10/2001
EP 1140061 B1 5/2003
EP 1316309 A1 6/2003
EP 2760911 B1 11/2017
EP 1434572 B1 12/2017
GB 922029 A 3/1963
GB 2295390 A 5/1996
JP S5742651 A 3/1982
JP S6212715 A 1/1987
JP H0449212 A 2/1992
JP H05508422 A 11/1993
JP H06508839 A 10/1994
JP H0753365 A 2/1995
JP H08511257 A 11/1996
JP H09104620 A 4/1997
JP H10505604 A 6/1998
JP 2001513552 A 9/2001
JP 2002533388 A 10/2002
JP 2004514732 A 5/2004
JP 2007521231 A 8/2007
JP 2008512386 A 4/2008
JP 2008519847 A 6/2008
JP 2008528571 A 7/2008
JP 2009532331 A 9/2009
JP 2011500865 A 1/2011
JP 2012507532 A 3/2012
RU 2210360 C1 8/2003
WO WO-9428880 A1 12/1994
WO WO-9640105 A1 12/1996
WO WO-9909972 A1 3/1999
WO WO-0038672 A2 7/2000
WO WO-0245684 A2 6/2002
WO WO-2005016318 A1 2/2005
WO WO-2005030174 A1 4/2005
WO WO-2005092336 A1 10/2005
WO WO-2005099671 A2 10/2005
WO WO-2006029155 A2 3/2006
WO WO-2006053186 A2 5/2006
WO WO-2006080029 A1 8/2006
WO WO-2007053698 A2 5/2007
WO WO-2007103200 A2 9/2007
WO WO-2008086804 A2 7/2008
WO WO-2009056550 A2 5/2009
WO WO-2010053691 A1 5/2010
WO WO-2010055260 A1 5/2010
WO WO-2010105673 A1 9/2010
WO WO-2011119839 A1 9/2011
WO WO-2011127252 A2 10/2011
WO WO-2011135461 A2 11/2011
WO WO-2011139271 A1 11/2011
WO WO-2011140310 A2 11/2011
WO WO-2012028688 A1 3/2012
WO WO-2012107652 A1 8/2012
WO WO-2014078014 A2 5/2014
WO WO-2014144027 A1 9/2014
WO WO-2015120006 A1 8/2015
WO WO-2015120110 A2 8/2015
WO WO-2015166473 A1 11/2015
WO WO-2015181059 A1 12/2015
WO WO-2016065481 A1 5/2016
WO WO-2016087952 A1 6/2016
WO WO-2016178132 A1 11/2016
WO WO-2017147375 A1 8/2017
WO WO-2017182851 A1 10/2017
WO WO-2018015563 A1 1/2018
WO WO-2019123269 A1 6/2019
WO WO-2020106735 A1 5/2020
WO WO-2020178695 A1 9/2020
WO WO-2021133778 A1 7/2021
WO WO-2021168403 A1 8/2021
WO WO-2022082105 A2 4/2022
WO WO-2023062018 A1 4/2023
WO WO-2023135150 A1 7/2023

OTHER PUBLICATIONS

Ali et al., "Idiopathic Hypersomnia: Clinical Features and Response to Treatment," Journal of Clinical Sleep Medicine, 2009, 5(6), 562-568.

Alshaikh et al., "Sodium Oxybate for Narcolepsy with Cataplexy: Systematic Review and Meta-Analysis," Journal of Clinical Sleep Medicine, 2012, vol. 8, No. 4, 451-458.

American Heart Association, "Why Should I Limit Sodium?" 2017, 2 pages, retrieved from https://www.heart.org/-/media/files/health-topics/answers-by-heart/why-should-i-limit-sodium.pdf.

Anand et al. "Ion-exchange resins: carrying drug delivery forward." Drug Discovery Today (2001); 6.17: 905-914.

Andersen et al., "Idiopathic Hypersomnia: A Study of 77 Cases," Sleep, 2007; 30(10):1274-1281.

Arena et al. "Absorption of sodium γ-hydroxybutyrate and its Prodrug γ-butyrolactone: Relationship between in vitro transport and in Vivo absorption." Journal of Pharmaceutical Sciences (1980); 69 (3): 356-358.

Baldrick, P., "Pharmaceutical excipient development: the need for preclinical guidance," Regulatory Toxicology and Pharmacology, Oct. 2000, 32(2), pp. 210-218.

Basetti and Aldrich, "Idiopathic hypersomnia. A series of 42 patients," Brain, (Aug. 1997) 120(8): 1423-1435.

Baumann et al., "Challenges in Diagnosing Narcolepsy without Cataplexy: A Consensus Statement," Sleep 2014;37(6):1035-1042.

Bedard, "Nocturnal γ-Hydroxybutyrate—Effect on Periodic Leg Movements and Sleep Organization of Narcoleptic Patients," Clin Neuropharmacol., 12(1), Feb. 1989, 29-36.

Berner, Jon E., "A Case of Sodium Oxybate Treatment of Tardive Dyskinesia and Bipolar Disorder," J. Clin. Psychiatry, 2008, 69:5, p. 862.

Berthier, et al., "Possible Involvement of a Gamma-Hydroxybutyric Acid Receptor in Startle Disease," Acta Paediatr, 83,1994, 678-680.

lliard and Sonka, "Idiopathic Hypersomnia: Historical Account, Critical Review of Current Tests and Criteria, Diagnostic Evaluation in the Absence of Biological Markers and Robust Electrophysiological Diagnostic Criteria," Nature and Science of Sleep 2022:14 311-322.

Billiard and Sonka, "Idiopathic hypersomnia," Sleep Medicine Reviews, Oct. 2016, vol. 29, pp. 23-33.

(56) References Cited

OTHER PUBLICATIONS

Billiard, M., Epidemiology of central disorders of hypersomnolence, Reference Module in Neuroscience and Biobehavioral Psychology, 2017, 9 pages.
Bodmeier, R., "Tableting of coated pellets," European Journal of Pharmaceutics and Biopharmaceutics, (1997) 43(1), 1-8.
Borgen et al., "The influence of gender and food on the pharmacokinetics of sodium oxybate oral solution in healthy subjects." J Clin Pharmacol. (2003); 43(1): 59-65.
Borgen et al., "The Pharmacokinetics of Sodium Oxybate Oral Solution following Acute and Chronic Administration to Narcoleptic Patients," Journal of Clinical Pharmacology, 2004; 44:253-257.
Borgen, L., et al. "Xyrem® (sodium oxybate): A Study of Dose Proportionality in Healthy Human Subjects." J. Clin. Pharmacol. (2000); 40: 1053.
Broughton, et al. "Effects of Nocturnal Gamma-Hydroxybutyrate on Sleep/Waking Patterns in Narcolepsy-Cataplexy." Can J. Neural Sci (1980); 7 (1): 23-31.
Broughton, et al. "Gamma-Hydroxy-Butyrate in the Treatment of Narcolepsy: a Preliminary Report." (1976) Narcolepsy, Ny, N.Y., Spectrum Publications, Inc. 659-668.
Broughton et al., "The Treatment of Narcolepsy-Cataplexy with Nocturnal Gamma-Hydroxybutyrate." Can J. Neural Sci (1979); 6(1): 1-6.
Caballero et al. "Characterization of alginate beads loaded with ibuprofen lysine salt and optimization of the preparation method." International Journal of Pharmaceutics (2014); 460.1: 181-188.
Chem Abstract ES302338, SciFinder, (1964), 1 pg.
Chemical Abstracts: Seventh Collective Index, vols. 56-65, (1962-1966), 4 pgs.
Chen et al, "Pharmacokinetics, relative bioavailability and food effect of JZP-258 and sodium oxybate: results of two phase 1, open-label, randomised crossover studies in healthy volunteers," Sleep Medicine, Abstracts, 2019, vol. 64, pp. S65-S66.
Ciccone, I., "Despite Missing Primary End Point, Pitolisant Shows Positive Outcomes in Phase 3 INTUNE Trial for Idiopathic Hypersomnia," NeurologyLive, Oct. 17, 2023, 5 pages, retrieved from https://www.neurologylive.com/view/despite-missing-primary-end-point-pitolisant-shows-positive-outcomes-phase-3-intune-trial-idiopathic-hypersomnia.
ClinicalTrials.gov Identifier NCT00087555, Trial Comparing the Effects of Xyrem (Sodium Oxybate) with Placebo for the Treatment of Fibromyalgia, Results First Posted Jan. 10, 2012, 9 pages, retrieved from https://www.clinicaltrials.gov/ct2/show/record/NCT00087555?term=oxybate&type=Intr&cond=Fibromyalgia&draw=2.
ClinicalTrials.gov Identifier: NCT02512588, A Study of Safety and Efficacy of BTD-001 in Treatment of Patients With Idiopathic Hypersomnia (IH) or Narcolepsy Type 2, First Posted—Jul. 31, 2015, Last Update Posted—Jan. 16, 2019, retrieved from https://clinicaltrials.gov/ct2/show/NCT02512588, 6 pages.
ClinicalTrials.gov Identifier: NCT0359755, Sodium Oxybate in Idiopathic Hypersomnia (SODHI), Latest Update—May 16, 2019, retrieved from: https://clinicaltrials.gov/ct2/history/NCT03597555?V_3=View#StudyPageTop, 9 pages.
Dauvilliers et al., "Clinical considerations for the diagnosis of idiopathic hypersomnia," Sleep Medicine Reviews 66 (2022) 101709, 10 pages.
Davis et al. "Active chloride secretion in the normal human jejunum." J Clin Invest. (1980); 66(6): 1326-1333.
Delrosso et al. "Manual Characterization of Sleep Spindle Index in Patients with Narcolepsy and Idiopathic Hypersomnia," Sleep Disorders, 2014, vol. 2014, Article ID 271802, 4 pages.
D'Souza et al., "A review of in vivo and in vitro aspects of alcohol-induced dose dumping" AAPS Open (2017) 3:5, 20 pages.
EROWID, "Gamma-hydroxybutyrate (GHB) Basic Synthesis Procedure," http://www.erowid.org/chemicals/ghb/ghb_synthesis.shtml (as downloaded on Aug. 8, 2013), 2 pages.
European Search Report issued Apr. 11, 2003 in European Application No. 03075658.9, 5 pages.
Evangelista et al., "Update on treatment for idiopathic hypersomnia," Expert Opinion on Investigational Drugs, 2018, 27(2), 187-192.
FDA, Xyrem® (sodium oxybate) oral solution label, Approved Labeling Text, Nov. 18, 2005, 59 pages.
Ferrara, S. D., et al., "Pharmacokinetics of Y-Hydroxybutyric Acid in Alcohol Dependent Patients After Single and Repeated Oral Doses." Br. J. Clin. Pharmacol. (1992); 34: 231-235.
Ferris, T.J., et al., "Synthesis, characterisation and detection of gamma-hydroxybutyrate salts," Forensic Science International, 2012, 216:158-162.
Fides, "Solutions of 4-hydroxybutyric acid salts for injection," Chem Abstract ES302338. Laboratorio M. Cuatecases, S.A., 2011. 2 pages.
Foldvary-Schaefer et al., "Calcium, Magnesium, Potassium, and Sodium Oxybates: Dose Titration and Transition from Sodium Oxybate in a Placebo-Controlled, Double-Blind, Randomized Withdrawal Study in Adult Participants with Narcolepsy with Cataplexy" Sleep 2020, the 34th Annual Meeting of the Associated Professional Sleep Societies (APSS) Aug. 27-30, 2020, Abstract ID: 0752, 1 page.
Frucht, et al. "A pilot Tolerability and Efficacy Trial of Sodium Oxybate in Ethanol-Responsive Movement Disorders." Movement Disorders (2005); 20 (10): 1330-1337.
Frucht, S.J., et al., "A Single-Blind, Open-Label Trial of Sodium Oxybate for Myoclonus and Essential Tremor," Neurology (2005); 65 (12): 1967-1970.
Fuller et al., "Effectiveness and Optimization of Low-Sodium Oxybate in Participants with Narcolepsy Switching from Sodium Oxybate: Final Data from the Substitution of Equal Grams of Uninterrupted Xyrem to Xywav (SEGUE) Study" Poster Presentation, 76th Annual Meeting of the American Academy of Neurology, Apr. 13-18, 2024, 1 page.
Gallimberti et al., "Clinical efficacy of gamma-hydroxybutyric acid in treatment of opiate withdrawal," Eur Arch Psychiatry Clin Neurosci. 1994;244(3):113-114.
Gallimberti et al., "Gamma-Hydroxybutyric Acid for Treatment of Opiate Withdrawal Syndrome," Neuropsychopharmacology, 1993, vol. 9, No. 1, pp. 77-81.
Gallimberti, L., "Gamma-hydroxybutyric Acid for Treatment of Alcohol Withdrawal Syndrome," The Lancet, 2(8666), (1989), 787-789.
Gallimberti, L., "Gamma-Hydroxybutyric Acid in the Treatment of Alcohol Dependence: A Double-Blind Study," Alcohol Clin. Exp. Res. (1992), 16(4): 673-676.
Geek Wench et al., "Title: Does anyone know why Jazz choose to make sodium oxybate?", Sep. 14, 2010: downloaded from http://www.talkaboutsleep.com/message-boards/topic/does-anybody-know-why-jazz-chose-to-make-sodium-oxybate/ on Nov. 13, 2017 (30 pages).
Geekwench et al., "Title: Does anyone know why Jazz choose to make sodium oxybate?", Sep. 14, 2010; downloaded from http://www.talkaboutsleep.com/message/boards/topic/does-anybodyknow-why-jazz-chose-to-make-sodium-oxybate/#sthash.no0PSCkL.dpuf on Jan. 21, 2015 (30 pages).
Germain et al., "Sleep-specific mechanisms underlying post-traumatic stress disorder: integrative review and neurobiological hypotheses," Sleep Med Rev 2008;12(3): 185-195 (16 pages).
Gerra, G., et al., "Flumazenil effects on growth hormone response to gamma-hydroxybutyric acid," Int Clin Psychopharmacol. (1994); 9 (3): 211-215.
Gessa, G. L., et al., "Gamma-hydroxybutyric acid (GHB) for treatment of ethanol dependence," European Neuropsychopharmacology, 3(3), (1993), 224-225.
Gessa, G. L., "Gamma-hydroxybutyric Acid in the Treatment of Alcohol Dependence," Clin. Neuropharm., vol. 15 Suppl. 1, Pt A, (1992), 303a-304a.
Grove-White, I. G., "Critical Flicker Frequency after Small Doses of Methohexitone, Diazepam and Sodium 4-Hydroxybutyrate." Brit. J. Anaesth (1971); 43 (2): 110-112.
Grove-White, I. G., et al., "Effect of Methohexitone, Diazepam and Sodium 4-Hydroxybutyrate on Short-Term Memory." Brit. J. Anaesth (1971); 43 (2): 113-116.

(56) References Cited

OTHER PUBLICATIONS

Guilleminault, et al., “Excessive daytime sleepiness: A challenge for the practicing neurologist” Brain (2001) 124: 1482-1491.
Harmony Biosciences, LLC, WAKIX® (pitolisant) tablets, for oral use, Highlights of Prescribing Information, Jun. 2024, 21 pages.
Hasenbos, M.A., et al., “Anaesthesia for bullectomy. A technique with spontaneous ventilation and extradural blockade.” Anaesthesia (1985); 40 (10): 977-980.
“HIB-IMUNE,” Physicians Desk Reference (41st ed.), (1987), 1095-1096.
“HibVAX,” Physicians Desk Reference (41st ed.), (1987), 870.
Hoes, M. J., “Gamma-hydroxybutyric acid (*) as hypnotic. Clinical and pharmacokinetic evaluation of gammahydroxybutyric acid as hypnotic in man,” L’Encephale: Revue de psychiatrie clinique biologique et therapeutique (1980); 6 (1): 93-99.
International Search Report and Written Opinion for International Application No. PCT/EP2022/078269 dated Jan. 31, 2023, 14 pages.
International Search Report and Written Opinion for International Application No. PCT/EP2023/050494 dated Apr. 17, 2023, 14 pages.
International Search Report and Written Opinion for International Application No. PCT/US2021/055426, mailed Apr. 11, 2022, 19 pages.
International Search Report and Written Opinion of the International Searching Authority for International Application No. PCT/US2019/062237, dated Mar. 31, 2020, 11 pages.
International Search Report and Written Opinion of the International Searching Authority for International Application No. PCT/US2020/066561, dated Apr. 13, 2021, 12 pages.
International Search Report and Written Opinion of the International Searching Authority for International Application No. PCT/US2021/019024, dated Jun. 2, 2021, 10 pages.
International Search Report and Written Opinion of the International Searching Authority for International Application No. PCT/US2021/054179, dated Jan. 17, 2022, 15 pages.
International Searching Authority, International Search Report and Written Opinion, mailed Jun. 27, 2018 for International Patent Application No. PCT/EP2018/056745 (12 pages).
International Searching Authority, International Search Report for International Application Serial No. PCT/US99/30740, mailed Jul. 21, 2000, 1 pg.
International Searching Authority, “International Search Report, mailed Apr. 15, 2014, for International Patent Application No. PCT/US2013/074954” 3 pages.
International Searching Authority, “Written Opinion, mailed Apr. 15, 2014, for International Patent Application No. PCT/US2013/074954” 8 pages.
Jazz Pharmaceuticals, Inc., “Xyrem® (sodium oxybate) oral solution, CIII,” Highlights of Prescribing Information, Revised, Sep. 2016, 31 pages.
Jazz Pharmaceuticals, Inc., “Xyrem® (sodium oxybate) oral solution, CIII,” Highlights of Prescribing Information, Revised, Sep. 2020, 35 pages.
Jazz Pharmaceuticals, Inc., “Xyrem® (sodium oxybate) oral solution Prescribing Information,” Xyrem® US Package Insert available at http://pp.jazzpliamia.com/pi/xyem.en.USPI.pdf (downloaded Sep. 12, 2017, 32 pages).
Jazz Pharmaceuticals, Inc., “Xywav® (calcium, magnesium, potassium, and sodium oxybates) oral solution, CIII,” Highlights of Prescribing Information, Aug. 2021, 40 pages.
Jazz Pharmaceuticals, “Jazz Pharmaceuticals Announces Positive Top-line Results from Phase 3 Study of JZP-258 in Adult Narcolepsy Patients with Cataplexy and Excessive Daytime Sleepiness,” Mar. 26, 2019, 2 pages, retrieved from https://investor.jazzpharma.com/node/16206/pdf.
Jazz Pharmaceuticals, “Xyrem® Dosing & Titrating Information for Adults | Xyrem® for HCPs”, May 9, 2021, 8 pages, retrieved from https://web.archive.org/web/20210509203007/https://www.xyremhcp.com/xyrem-dosing-and-titrating-adults.
Jennum et al., “Comorbidity and Mortality of Narcolepsy: A Controlled Retro- and Prospective National Study,” Sleep 2013;36(6):835-840.
Jha, M.K, “Modified release formulations to achieve the quality target product profile (QTPP),” IJPSR, 2012; vol. 3(8): 2376-2386.
Karppanen and Mervaala, “Sodium intake and hypertension”, Progress in Cardiovascular Diseases, Sep.-Oct. 2006, vol. 49, Issue 2, pp. 59-75.
Keating, GM, “Sodium Oxybate: A Review of Its Use in Alcohol Withdrawal Syndrome and in the Maintenance of Abstinence in Alcohol Dependence,” Clinical Drug Investigation (2014) 34, 63-80.
Khan and Trotti, “Central Disorders of Hypersomnolence: Focus on the Narcolepsies and Idiopathic Hypersomnia,” Chest, Jul. 2015, 148(1): 262-273.
Khediri et al., “Efficacy of Diosmectite (Smecta)® in the Treatment of Acute Watery Diarrhea in Adults: A Multicenter, Randomized, Double-Blind, Placebo-Controlled, Parallel Group Study,” Hindawi Publishing Corporation, Gastroenterology Research and Practice, 2011, vol. 2011, Article ID 783196, 8 pages.
Kim et al., “Different fates of excessive daytime sleepiness: survival analysis for remission,” Acta Neurologica Scandinavica, 2016, 134(1):35-41.
Laborit, H., “Gamma-Hydroxybutyrate, Succinic Semialdehyde and Sleep,” Laboratoire d’Eutonologie, (1973), 257-274.
Ladinsky, H., et al., “Mode of Action of Gamma-Butyrolactone on the Central Cholinergic System, Naunyn-Schmiedeberg’s,” Arch. Pharmacol. (1983); 322 (1): 42-48.
Lammers, G. J., “Gammahydroxybutyrate and Narcolepsy: A Double-Blind Placebo-Controlled Study.” Sleep (1993); 16 (3): 216-220.
Lapierre et al., “The Effect of Gamma-Hydroxybutyrate: A Double-Blind Study of Normal Subjects,” Sleep Research (1988); 17:99, 1988, 6 pages. (Abstract Only).
Lapierre, O., “The Effect of Gamma-Hydroxybutyrate on Nocturnal and Diurnal Sleep of Normal Subjects: Further Considerations on REM Sleep-Triggering Mechanisms.” Sleep (1990); 13 (1): 24-30.
Lavault et al., “Benefit and risk of modafinil in idiopathic hypersomnia vs. narcolepsy with cataplexy,” Sleep Medicine, 2011, 12(6), 550-556.
Lee, C. R., “Evidence for the β-oxidation of orally administered 4-hydroxybutyrate in humans.” Biochemical Medicine (1977); 17 (3): 284-291.
Lettieri and Fung, “Improved pharmacological activity via pro-drug modification: comparative pharmacokinetics of sodium gamma-hydroxybutyrate and gamma- butyrolactone.” Research Communications in Chemical Pathology and Pharmacology (1978); 22 (1): 107-118.
Leu-Semenescu et al., “Benefits and risk of sodium oxybate in idiopathic hypersomnia versus narcolepsy type 1: a chart review,” Sleep Medicine, Jan. 2016, vol. 17, pp. 38-44.
Leu-Semenescu et al., “Effects of pitolisant, a histamine H3 inverse agonist, in drug-resistant idiopathic and symptomatic hypersomnia: a chart review,” Sleep Medicine, Jun. 2014, vol. 15, Issue 6, pp. 681-687.
Lopez et al., “French consensus. Management of patients with hypersomnia: Which strategy?” Revue Neurologique (Paris), 2017, 173(1-2): 8-18.
Lubrano, et al. “Fibromyalgia in Patients with Irritable Bowel Syndrome. An Association with the Severity of the Intestinal Disorder.” Int J Colorectal Dis. (2001); 16 (4): 211-215.
Luhn, O., “Using Excipients In Powder Formulations,” Pharmaceutical Technology Europe, Jan. 7, 2011, vol. 23, Issue 1, 6 pages, retrieved from https://www.pharmtech.com/view/using-excipients-powder-formulations.
Mahore et al. “Ion exchange resins: pharmaceutical applications and recent advancement.” Int J Pharm Sci Rev Res (2010); 1.2: 8-13.
Maitre, “The γ-hydroxybutyrate Signalling System in Brain Organization and Functional Implications,” Progress in Neurobiology, 51:337-361, 1997.
“Malic Acid,” The Handbook of Pharmaceutical Excipients, 2nd Ed., (1994 ), pp. 285-286, 633.
Mamelak, et al. The Effects of γ-Hydroxybutyrate on Sleep. Biol Psych (1977); 12 (2): 273-288.

(56) References Cited

OTHER PUBLICATIONS

Mamelak, M., et al., "Treatment of Narcolepsy and Sleep Apnea with Gammahydroxybutyrate: A clinical and polysomnographic case study." Sleep (1981); 4 (1): 105-111.
Mamelak, M., et al., "Treatment of Narcolepsy with y-hydroxybutyrate. A review of Clinical and Sleep Laboratory Findings." Sleep (1986); 9 (1): 285-290.
Mamelak, M., "Gammahydroxybutyrate: An endogenous regulator of energy metabolism." Neuroscience and Biobehavioral Reviews (1989); 13 (4): 187-198.
Mamelak, M., "Sleep-Inducing Effects of Gammahydroxybutyrate." The Lancet (1973); 302 (7824): 328-329.
Manalac, T., "FDA Kicks Down Harmony's Bid to Push Wakix Into Idiopathic Hypersomnia," BioSpace, Feb. 20, 2025, 3 pages, retrieved from https://www.biospace.com/fda/fda-kicks-down-harmonys-bid-to-push-wakix-into-idiopathic-hypersomnia.
Markman Opinion, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES, 21 pages.
Maski et al., "Treatment of central disorders of hypersomnolence: an American Academy of Sleep Medicine clinical practice guideline," Journal of Clinical Sleep Medicine, Sep. 1, 2021, vol. 17, No. 9, pp. 1881-1893.
Medicines for Children, "Oral Rehydration Salts," Leaflet information published Jul. 25, 2013, by Neonatal and Paediatric Pharmacists Group (NPPG), 6 pages, retrieved from https://www.medicinesforchildren.org.uk/oral-rehyd ration-salts.
Meskill et al., "Asymmetric And/or Atypical Dosing Of Sodium Oxybate May Lead To Increased Compliance And Efficacy," Sleep, Apr. 2019, vol. 42, Abstract Supplemental, 0606, p. A241.
Mignot, E.J.M., "A Practical Guide to the Therapy of Narcolepsy and Hypersomnia Syndromes," Neurotherapeutic, 2012, 9(4), 739-752.
Moldofsky et al. "A Chronobiologic Theory of Fibromyalgia." J. Muscoloskel. Pain, 1, 49 (1993).
Moldofsky et al., "Effects of Sodium Oxybate on Sleep Physiology and Sleep/Wake-related Symptoms in Patients with Fibromyalgia Syndrome: A Double-blind, Randomized, Placebo-controlled Study," Journal of Rheumatology, Aug. 3, 2010, vol. 37(10), pp. 2156-2166.
Moldofsky, et al. "Musculoskeletal Symptoms and Non-REM Sleep Disturbance in Patients with 'Fibrositis Syndrome' and Healthy Subjects." Psychosom. Med. (1975); 37 (4): 341-351.
Montplaisir J, Barbezieux EM. Le gamma-hydroxybutyrate de sodium (GHB) dans le traitement de l'hypersomnie essentielle. The Canadian Journal of Psychiatry. 1981;26(3):162-166 (with English translation, 11 pages).
Morgenthaler et al., "Practice Parameters for the Treatment of Narcolepsy and other Hypersomnias of Central Origin," Sleep, 2007, 30(12): 1705-1711.
Morrison, Robert T., et al., "Organic Chemistry", Chapter 20: "Functional Derivatives of Carboxylic Acids," 3rd Edition, 1973, pp. 658-700.
Morrison, Robert Thornton, et al., Organic Chemistry, 3rd Edition, (1973), pp. 672-677.
Nema, S, et al., "Excipients and Their Use in Injectable Products." PDA J. Pharm. Sci. Technol. (1997); 51(4): 166-171.
Neuman, Ariel, "GHB's Path to Legitimacy: An Administrative and Legislative History of Xyrem." Apr. 2004, Harvard Law School, Class of 2005, Food and Drug Law, Winter Term 2004, Professor Peter Barton Hutt. (2004), 1-39.
Nittur et al., "Mazindol in narcolepsy and idiopathic and symptomatic hypersomnia refractory to stimulants: A long-term chart review," Sleep Medicine, 2013, 14(1), 30-36.
Ohayon et al., "Sodium Oxybate Dosing Utilization Patterns in the Nexus Narcolepsy Registry," Sleep, Apr. 2019, vol. 42, Abstract Supplemental, 0605, p. A241.
Ohayon, M.M., "Narcolepsy is complicated by high medical and psychiatric comorbidities: a comparison with the general population," Sleep Medicine, Jun. 2013, 14(6):488-492.
Ohta et al. "Development of a simple method for the preparation of a silica gel based controlled delivery system with a high drug content." European Journal of Pharmaceutical Sciences (2005); 26.1: 87-96.
Okun et al., "GHB: An Important Pharmacologic and Clinical Update", J. Pharm Pharmaceut. Sci. 2001, 4(2): 167-175.
Ondo, William G., et al., "Sodium Oxybate for Excessive Daytime Sleepiness in Parkinson's Disease: A Polysomnographic Study." Arch. Neural. (2008); 65 (10): 1337-1340.
Oosterloo et al., "Possible confusion between primary hypersomnia and adult attention-deficit/hyperactivity disorder," Psychiatry Res. (2006) 143(2-3): 293-297.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil1 0-6108 ES), (Sep. 14, 2012) 1 page.
Outlaw, et al. "Dyspepsia and its Overlap with Irritable Bowel Syndrome." Curr Gastroenterol Rep. (2006); 8 (4): 266-272.
Ozaki et al., "Health-Related Quality of Life Among Drug-Naïve Patients with Narcolepsy with Cataplexy, Narcolepsy Without Cataplexy, and Idiopathic Hypersomnia Without Long Sleep Time," Journal of Clinical Sleep Medicine, 4(6), 572-578.
Palatini, P., "Dose Dependent Absorption and Elimination of Gamma-Hydroxybutyric Acid in Healthy Volunteers." Eur. J. Clin. Pharmacol. (1993); 45 (4): 353-356.
Pardi and Black, "γ-Hydrobutyrate/Sodium Oxybate: neurobiology, and impact on Sleep and Wakefulness," CNS Drugs, 2006, 20(12): 993-1018.
Parmar et al., "Clinical Characteristics of Cataplectic Attacks in Type 1 Narcolepsy," Current Neurology and Neuroscience Reports (2020) 20:38, 9 pages.
Pascoe et al., "Effects of Pharmacotherapy Treatment on Patient-Reported Outcomes in a Narcolepsy and Idiopathic Hypersomnia Cohort," J Clin Sleep Med., Dec. 15, 2019; 15(12):1799-1806.
Patil et al. "A review on ionotropic gelation method: novel approach for controlled gastroretentive gelispheres." International Journal of Pharmacy and Pharmaceutical Sciences (2012); 4.4: 27-32.
Perucca, E., "Clinically relevant drug interactions with antiepileptic drugs," Br J Clin Pharmacol, 2005, 61:3 246-255.
Philip et al., "Is there a link between subjective daytime somnolence and sickness absenteeism? A study in a working population," J. Sleep Res. (2001) 10, 111-115.
"Phospholine Iodide," Physicians Desk Reference (50th ed.), (1996), 2784.
Pizza et al., "Car Crashes and Central Disorders of Hypersomnolence: A French Study," PLoS ONE, (2015) 10(6):e0129386, 14 pages.
Pizza et al., "Polysomnographic study of nocturnal sleep in idiopathic hypersomnia without long sleep time," J Sleep Res. (2013) 22, 185-196.
Puguan et al. "Diffusion characteristics of different molecular weight solutes in Ca-alginate gel beads." Colloids and Surfaces A: Physicochemical and Engineering Aspects (2015); 469: 158-165.
Remington. The Science and Practice of Pharmacy. 20th Edition, Gennaro, Ed,. Lippincott Williams & Wilkins (2000). (p. 861).
Remington. The Science and Practice of Pharmacy. 20th Edition, Gennaro, Ed,. Lippincott Williams & Wilkins. Chapter 45 (Oral Solid Dosage Forms) (2000) 41 pages.
Response filed Feb. 16, 2001 to Written Opinion issued Oct. 18, 2000 in International Application No. PCT/US99/30740, 10 pages.
Rohm and Haas, "Amberlite® IRN78 Industrial Nuclear Grade Strong Base Anion Resin," 2000, PDS 0547—Jan. 1998, 2 pages.
Rohm and Haas. "Duolite AP143/1083 Pharmaceutical Grade Anion Exchange Resin." Feb. 2006, 4 pages.
Rosiaux Y, et al., "Ethanol-resistant polymeric film coatings for controlled drug delivery", Journal of Controlled Release, Jul. 2013, vol. 169, pp. 1-9.
Ross et al., "Sleep Disturbance as the Hallmark of Posttraumatic Stress Disorder," Am J Psychiatry, Jun. 1989, 146(6):697-707.
Rotem et al., "Polysomnographic and Actigraphic Evidence of Sleep Fragmentation in Patients with Irritable Bowel Syndrome," Sleep, 2003, vol. 26, No. 6, pp. 747-752.
Roth et al., "Hypersomnia With 'Sleep Drunkenness'," Archives of General Psychiatry, 1972, 26(5), 456-462.

(56) References Cited

OTHER PUBLICATIONS

Roth, et al., "γ-Butyrolactone and γ-Hydroxybutyric Acid-I, Distribution and Metabolism." Biochemical Pharmacology (1966); 15 (9):1333-1348.
Roth, R. H., et al., "γ-Butyrolactone and γ-Hydroxybutyric acid-II. The Pharmacologically active form." J. Neuropharmacol. (1966); 5 (6): 421-428.
Roxane Laboratories, Inc.'s Answer, Affirmative Defenses and Counterclaims to Plaintiff's Complaint, (Dec. 29, 2010) 21 pages.
Roxane Laboratories, Inc.'s Answer, Affirmative Defenses and Counterclaims to Plaintiff's Complaint, (Jun. 1, 2011) 12 pages.
Roxane Laboratories, Inc.'s Answer, Affirmative Defenses and Counterclaims to Plaintiff's Complaint, (Mar. 9, 2011) 13 pages.
Roxane Laboratories, Inc.'s Answer, Affirmative Defenses and Counterclaims to Plaintiff's Complaint, (Nov. 9, 2012) 18 pages.
Roxane Laboratories, Inc.'s Answer and Affirmative Defenses to Plaintiff's Complaint, (Jan. 4, 2013) 8 pages.
Roxane Laboratories, Inc.'s Initial Invalidity and Noninfringement Contentions Pursuant to Local Patent Rule 3.6, (Apr. 14, 2011) 317 pages.
Roy et al., "Sodium oxybate prescribing adjustments by physicians in a real world clinical setting," Sleep Medicine, Dec. 2019, vol. 64, Supplement 1, pp. S329-S330.
Rubbens et al., "Gastric and Duodenal Ethanol Concentrations after intake of Alcoholic Beverages in Postprandial Conditions," Molecular Pharmaceutics, (2017) 14(12):4202-4208.
Rujivipat et al., "Improved drug delivery to the lower intestinal tract with tablets compression-coated with enteric/nonenteric polymer powder blends," European Journal of Pharmaceutics and Biopharmaceutics (2010) 76: 486-492.
Russell, I. Jon, et al., "Sodium Oxybate Relieves Pain and Improves Function in Fibromyalgia Syndrome." Arthritis. Rheum. (2009); 60 (1): 299-309.
Saini and Rye, "Hypersomnia: Evaluation, Treatment, and Social and Economic Aspects," Sleep Medicine Clinics, (2017) 12(1), 47-60.
Sandson, N. et al., "An Interaction Between Aspirin and Valproate: The Relevance of Plasma Protein Displacement Drug-Drug Interactions", Am J Psychiatry Nov. 2006, 163:11, 1891-1896.
Scharf, et al., "Effect of Gamma-Hydroxybutyrate on Pain, Fatigue, and the Alpha Sleep Anomaly in Patients with Fibromyalgia," (1998) J. Rheumatol. (1998) 25:1986-1990.
Scharf, M. B et al."GHB-New Hope for Narcoleptics?" Biol Psychiatry (1989); 26 (4): 329-330.
Scharf, M. B "The Effects and Effectiveness of γ-Hydroxybutyrate in Patients with Narcolepsy." J. Clin. Psychiatry (1985); 46 (6): 222-225.
Scharf, Martin B et al., "The Effects of Sodium Oxybate on Clinical Symptoms and Sleep Patterns in Patients with Fibromyalgia." J. Rheumatol. (2003); 30 (5): 1070-1074.
Scrima, et al., "Effect of Gamma-Hydroxybutyrate on a Patient with Obstructive Sleep Apnea." Sleep Research (1987); 16: 137.
Scrima, et al., "Effect of High Altitude on a Patient with Obstructive Sleep Apnea." Sleep Research (1987); 16: 427.
Scrima, et al., "Effects of Gamma-Hydroxybutyrate (GHB) on Narcolepsy-Cataplexy Symptoms and MSLT Results in Male and Female Patients." Association of Professional Sleep Societies (1988); 251.
Scrima, et al., "Gamma-Hydroxybutyrate Effects on Cataplexy and Sleep Attacks in Narcoleptics." Sleep Research (1987); 16: 134.
Scrima, L., et al., "Efficacy of Gamma-Hydroxybutyrate Versus Placebo in Treating Narcolepsy-Cataplexy: Double-Blind Subjective Measures," Biol. Psychiatry (1989); 26 (4): 331-343.
Scrima, L., et al., "Narcolepsy." New England J. Med. (1991); 324 (4): 270-272.
Scrima, L., "The Effects of γ-Hydroxybutyrate on the Sleep of Narcolepsy Patients: A Double-Blind Study." Sleep (1990); 13 (6): 479-490.
Seno and Yamabe. "The Rheological Behavior of Suspensions of lon-exchange Resin Particles." Bulletin of the Chemical Society of Japan (1966); 39.4: 776-778.
Series, F., "Effects of Enhancing Slow-Wave Sleep by Gamma-Hydroxybutyrate on Obstructive Sleep Apnea." Am. Rev. Respir. Dis. (1992); 145 (6): 1378-1383.
Shah et al., "In vitro Dissolution Profile Comparison—Statistics and Analysis of the Similarity Factor, f2," Pharm Research, (1998) 15(6):889-896.
Shinno et al., "Successful treatment with levothyroxine for idiopathic hypersomnia patients with subclinical hypothyroidism," General Hospital Psychiatry, 2009, 31(2), 190-193.
Singh et al. "Ion exchange resins: drug delivery and therapeutic applications." Fabad J. Pharm. Sci (2007); 32: 91-100.
Snead, et al., "Ontogeny of γ-Hydroxybutyric Acid. I. Regional Concentration in Developing Rat, Monkey and Human Brain." Brain Res. (1981); 227 (4): 579-589.
Snead, O. Carter, "γ-Hydroxybutyrate Model of Generalized Absence Seizures: Further Characterization and Comparison with Other Absence Models." Epilepsia (1988); 29 (4): 361-368.
Srikanth et al., "Ion-exchange resins as controlled drug delivery carriers." Journal of Scientific Research (2010); 2.3: 597-611.
Stock, G., "Increase in brain dopamine after axotomy or treatment with Gammahydroxybutyric acid due to elimination of the nerve impulse flow." Naunyn-Schmiedeberg's Arch. Pharmacol. (1973); 278 (4): 347-361.
Strong, A.J., "γ-Hydroxybutyric acid and intracranial pressure." The Lancet (1984); 1 (8389): 1304.
Suner, Selim, et al., "Pediatric Gamma Hydroxybutyrate Intoxication." Acad Emerg. Med. (1997); 4 (11): 1041-1045.
Taft et al., "Initial Assessment of Post-traumatic Stress in a US Cohort of Inflammatory Bowel Disease Patients," Inflamm. Bowel Dis., Sep. 2019, vol. 25, No. 9, pp. 1577-1585.
Takka and Gürel, "Evaluation of chitosan/alginate beads using experimental design: formulation and in vitro characterization." AAPS PharmSciTech (2010); 11.1: 460-466.
"Taxotere," Physicians Desk Reference (51st ed.), (1997), 2204-2207.
The Dow Chemical Company, Product Data Sheet for Amberlite IRN78 Resin. Form No. 177-02230-0311, Rev. 0, 3 pages, date unknown.
Thorpy et al., "Clinical considerations in the treatment of idiopathic hypersomnia," Sleep Medicine (2024) 119: 488-498.
Thorpy, M.J., "Recently Approved and Upcoming Treatments for Narcolepsy," CNS Drugs (2020) 34:9-27.
Thorpy M.J., "Update on Therapy for Narcolepsy," Curr Treat Options Neurol, (2015) 17:20, 12 pages.
Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012) 231 pages.
Trotti et al., "Flumazenil for the Treatment of Refractory Hypersomnolence: Clinical Experience with 153 Patients," J Clin Sleep Med 2016; 12(10): 1389-1394.
Trotti et al., "Improvement in daytime sleepiness with clarithromycin in patients with GABA-related hypersomnia: Clinical experience," J Psychopharmacol. 2014, 28(7): 697-702.
Trotti, L.M., "Idiopathic Hypersomnia," Sleep Medicine Clinics, 2017, 12(3): 331-344.
Tunnicliff, Godfrey, "Sites of Action of Gamma-Hydroxybutyrate (GHB)—A Neuroactive Drug with Abuse Potential." Clinical Toxicology (1997); 35 (6): 581-590.
Turnberg, L.A. "Abnormalities in intestinal electrolyte transport in congenital chloridorrhoea." Gut. (1971); 12(7): 544-551.
United States Pharmacopeial Convention, Inc.: The National Formulary, 23/NF18, (1995), p. 2205.
Unknown author, "How Much Protein Is In Your Cup of Milk?" downloaded from https://milklife.com/articles/nutrition/how-much-protein-your-cup-milk , 8 ounces of whole milk on Aug. 20, 2021, 2 pages. (Year: 2021).
Unknown author, title: definition of biotransformation; Medical dictionary; downloaded Jun. 21, 2018 (Year: 2018) 3 pages.

(56) References Cited

OTHER PUBLICATIONS

U.S. Department of Agriculture et al., "Dietary Guidelines for Americans 2010", 2010, 7th Edition, Washington, DC: U.S. Government Printing Office, Dec. 2010, 112 pages.
U.S. Department of Health and Human Services et al., "Dissolution Testing of Immediate Release Solid Oral Dosage Forms," Food and Drug Administration, CDER, Aug. 1997, 17 pages.
U.S. Department of Health and Human Services et al., "Extended Release Oral Dosage Forms: Development, Evaluation, and Application of In Vitro/In Vivo Correlations", Food and Drug Administration, CDER, Sep. 1997, 27 pages.
U.S. Department of Health and Human Services et al., "Guidance for Industry Food-Effect Bioavailability and Fed Bioequivalence Studies", Food and Drug Administration, CDER, Dec. 2002, BP, 12 pages.
U.S. Department of Health and Human Services et al., "Guidance for Industry SUPAC-MR: Modified Release Solid Oral Dosage Forms", Food and Drug Administration, CDER, Sep. 1997, CMC 8, 52 pages.
U.S. Department of Health and Human Services et al., "Statistical Approaches to Establishing Bioequivalence", Food and Drug Administration, CDER, Jan. 2001, BP, 48 pages.
Van Den Bogert, A. G., et al., "Placentatransfer of 4-hydroxybutyric acid in man," Anaesthesiology and Intensive Care Medicine (1978); 110: 55-64.
Vernet et al., "Subjective symptoms in idiopathic hypersomnia: beyond excessive sleepiness," Sleep Res. (2010) 19, 525-534.
Vickers, M.D., "Gammahydroxybutyric Acid." Int. Anesth. Clinic (1969); 7 (1): 75-89.
Vogel et al., "Toxicologic/transport properties of NCS-382, a γ-hydroxybutyratc (GHB) receptor ligand, in neuronal and epithelial cells: Therapeutic implications for SSADH deficiency, a GABA metabolic disorder," Toxicol In Vitro, 2018, 46:203-212 (Epub 2017).
Walden et al., "The Effect of Ethanol on the Release of Opioids 30 from Oral Sustained-Release Preparations," Drug Development and Industrial Pharmacy, 2007, 33:10, 1101-1111.
Walsh et al., "Enhancing Slow Wave Sleep with Sodium Oxybate Reduces the Behavioral and Physiological Impact of Sleep Loss", Sleep, Sep. 2010, 33(9), 1217-1225.
Wang, B. et al., "Diagnosis and Treatment of Sleep and Respiratory Disorders," Military Medical Science Press, Sep. 30, 2002, pp. 193-194, and English translation, 6 pages.
Waszkielewicz and Bojarski, "γ-Hydrobutyric Acid (GHB) and its Chemical Modifications: A Review of the GHBergic System," Pol. J. Pharmacol., 2004, 56, 43-49.
Wermuth (Ed.), The Practice of Medicinal Chemistry, Academic Press, Third Edition, "Preparation of Water-Soluble Compounds Through Salt Formulation," Chapter 37, 2008, p. 758, 6 pages.
World Health Organization, "Annex 7: Multisource (generic) pharmaceutical products: guidelines on registration requirements to establish interchangeability," WHO Expert Committee on Specifications for Pharmaceutical Preparations Fortieth Report, pp. 347-390, 2006, retrieved from http://apps.who.int/prequal/info_general/documents/TRS937/WHO_TRS_937_eng.pdf#page=359.
Xyrem Product information, Sep. 8, 2015, retrieved from the Internet: https://www.ema.europa.eu/en/documents/product-information/yrem-epar-product-information_en.pdf [retrieved on Jan. 6, 2022], pp. 1-36.
Yamada, Y., "Effect of Butyrolactone and Gamma-Hydroxybutyrate on the EEG and Sleep Cycle in Man," Electroencephalography and Clinical Neurophysiology (1967); 22 (6): 558-562.
Zhang et al., "Sleep in posttraumatic stress disorder: A systematic review and meta-analysis of polysomnographic findings," Sleep Medicine Reviews (2019) 48: 101210, 18 pages.
Zheng (Ed.), "Formulation and Analytical Development for Low-Dose Oral Drug Products," John Wiley & Sons, Inc., Hoboken, New Jersey, Table 4.1, p. 65, 2009, 3 pages.

* cited by examiner

SODIUM OXYBATE TO TREAT IDIOPATHIC HYPERSOMNIA

CROSS-REFERENCE TO RELATED APPLICATIONS

This application is a U.S. National Stage Application under 35 U.S.C. § 371 of International Application No. PCT/US2021/054179, filed Oct. 8, 2021, which claims the benefit of priority to U.S. Provisional Application No. 63/089,428 filed Oct. 8, 2020, the contents of which are hereby incorporated by reference in their entireties for all purposes.

BACKGROUND

Gamma-hydroxybutyrate (GHB), also known as "oxybate," is an endogenous compound that is found in many human body tissues. GHB is present, for example, in the mammalian brain and other tissues. In the brain, the highest GHB concentration is found in the hypothalamus and basal ganglia and GHB is postulated to function as an inhibitory neurotransmitter (Snead and Morley, 1981, Brain Res. 227 (4): 579-89). The neuropharmacologic effects of GHB include increases in brain acetylcholine, increases in brain dopamine, inhibition of GABA-ketoglutarate transaminase and depression of glucose utilization, but not oxygen consumption in the brain. GHB treatment substantially reduces the signs and symptoms of narcolepsy, i.e., daytime sleepiness, cataplexy, sleep paralysis, and hypnagogic hallucinations. In addition, GHB increases total sleep time and REM sleep, and it decreases REM latency, reduces sleep apnea, and improves general anesthesia (see U.S. Pat. Nos. 6,472,431; 6,780,889; 7,262,219; 7,851,506; 8,263,650; and 8,324,275, the disclosure of each of which is incorporated by reference in its entirety for all purposes).

Idiopathic hypersomnia (IH) is a rare disorder of central hypersomnolence characterized by severe excessive daytime sleepiness (EDS) occurring almost daily for at least 3 months, and timing of nocturnal sleep. Patients with IH face many disorder-associated challenges such as difficulty securing and sustaining employment, altered cognition, attention deficit, symptoms of autonomic dysfunction (faintness, difficulties in regulating body temperature, headaches and palpitations) and significant safety risks when operating a motor vehicle.

There is a need in the art for methods of treating IH.

SUMMARY

In one aspect, the present disclosure provides methods of treating idiopathic hypersomnia using oxybate, preferably sodium oxybate or a mixture of salts of oxybate (a mixed salt oxybate). In some embodiments, the mixed salt oxybate comprises one or more of the following: calcium, sodium, potassium, and magnesium salts.

In some embodiments, the mixed salt oxybate comprises about 8% sodium oxybate, about 23% potassium oxybate, about 21% magnesium oxybate and about 48% calcium oxybate (mol. equiv. %).

In some embodiments, about 0.5 g-9 g of the sodium oxybate is administered per day. In some embodiments, about 0.5 g of the sodium oxybate is administered per day. In some embodiments, about 0.25 g of the sodium oxybate is administered twice per day. In some embodiments, about 0.17 g of the sodium oxybate is administered three times per day. In some embodiments, about 1.0 g of the sodium oxybate is administered per day. In some embodiments, about 0.5 g of the sodium oxybate is administered twice per day. In some embodiments, about 0.33 g of the sodium oxybate is administered three times per day. In some embodiments, about 1.5 g of the sodium oxybate is administered per day. In some embodiments, about 0.75 g of the sodium oxybate is administered twice per day. In some embodiments, about 0.50 g of the sodium oxybate is administered three times per day. In some embodiments, about 2.0 g of the sodium oxybate is administered per day. In some embodiments, about 1.0 g of the sodium oxybate is administered twice per day. In some embodiments, about 0.66 g of the sodium oxybate is administered three times per day. In some embodiments, about 2.5 g of the sodium oxybate is administered per day. In some embodiments, about 2.5 g of the sodium oxybate is administered once per day. In some embodiments, about 1.25 g of the sodium oxybate is administered twice per day. In some embodiments, about 0.83 g of the sodium oxybate is administered three times per day. In some embodiments, about 3.0 g of the sodium oxybate is administered per day. In some embodiments, about 3.0 g of the sodium oxybate is administered once per day. In some embodiments, about 1.5 g of the sodium oxybate is administered twice per day. In some embodiments, about 1.0 g of the sodium oxybate is administered three times per day. In some embodiments, about 3.5 g of the sodium oxybate is administered per day. In some embodiments, about 3.5 g of the sodium oxybate is administered once per day. In some embodiments, about 1.75 g of the sodium oxybate is administered twice per day. In some embodiments, about 1.16 g of the sodium oxybate is administered three times per day. In some embodiments, about 4.0 g of the sodium oxybate is administered per day. In some embodiments, about 4.0 g of the sodium oxybate is administered once per day. In some embodiments, about 2.0 g of the sodium oxybate is administered twice per day. In some embodiments, about 1.32 g of the sodium oxybate is administered three times per day. In some embodiments, about 4.5 g of the sodium oxybate is administered per day. In some embodiments, about 4.5 g of the sodium oxybate is administered once per day. In some embodiments, about 2.25 g of the sodium oxybate is administered twice per day. In some embodiments, about 1.5 g of the sodium oxybate is administered three times per day. In some embodiments, about 5 g of the sodium oxybate is administered per day. In some embodiments, about 5 g of the sodium oxybate is administered once per day. In some embodiments, about 2.5 g of the sodium oxybate is administered twice per day. In some embodiments, about 5.5 g of the sodium oxybate is administered per day. In some embodiments, about 5.5 g of the sodium oxybate is administered once per day. In some embodiments, about 2.75 g of the sodium oxybate is administered twice per day. In some embodiments, about 6 g of the sodium oxybate is administered per day. In some embodiments, about 6 g of the sodium oxybate is administered once per day. In some embodiments, about 3.0 g of the sodium oxybate is administered twice per day. In some embodiments, about 2.0 g of the sodium oxybate is administered three times per day. In some embodiments, about 7.5 g of the sodium oxybate is administered per day. In some embodiments, about 3.75 g of the sodium oxybate is administered twice per day. In some embodiments, about 2.5 g of the sodium oxybate is administered three times per day. In some embodiments, about 9.0 g of the sodium oxybate is administered per day. In some embodiments, about 4.5 g of the sodium oxybate is administered twice per day. In some embodiments, about 3.0 g of the sodium oxybate is administered three times per day.

In some embodiments, the sodium oxybate is administered when the patient wants to go to sleep. In some embodiments, the sodium oxybate is administered at bedtime and about 2.5 h-4 h after the bedtime administration. In some embodiments, the sodium oxybate is administered after a period of sleep.

In some embodiments, sodium oxybate is in a liquid. In some embodiments, the concentration of the mixed salt in the liquid is about 0.5 g/mL. In other embodiments, sodium oxybate is a solid.

DEFINITIONS

Figure 1:
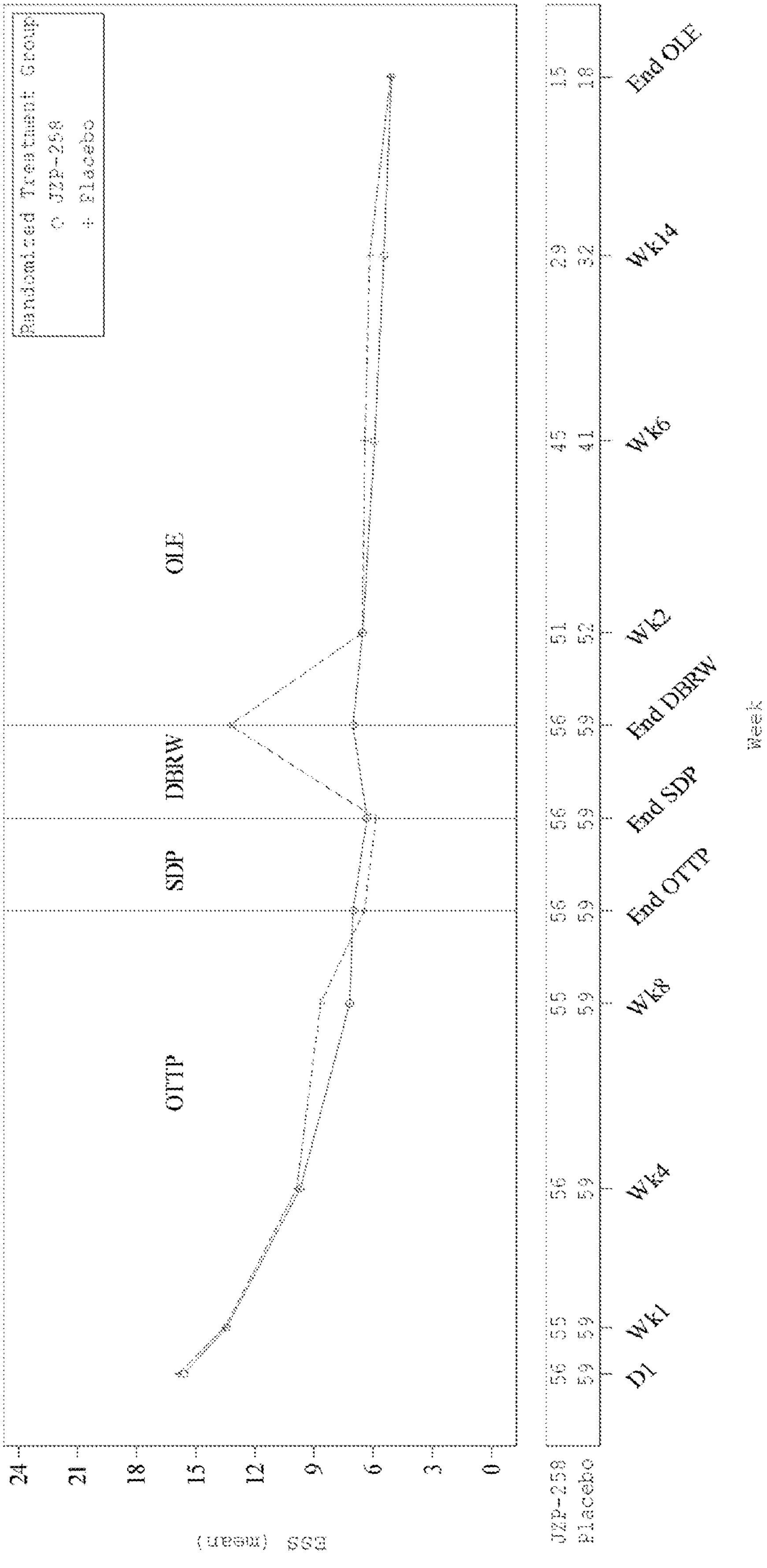
FIG. 1 shows the change in mean Epworth Sleepiness Scale (ESS) score during the study described in Example 1 for patients treated with JZP-258 and patients treated with placebo.

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms "administer," "administering" or "administration" as used herein refer to administering a compound or pharmaceutically acceptable salt of the compound or a composition or formulation comprising the compound or pharmaceutically acceptable salt of the compound to a patient.

As used herein, the term "gamma-hydroxybutyrate" (GHB) or "oxybate" refers to the negatively charged or anionic form (conjugate base) of gamma-hydroxybutyric acid. GHB has the following structural formula:

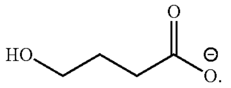

As used herein, the term "gamma-hydroxybutyric acid" (GBA) refers to the protonated form (conjugate acid) of gamma-hydroxybutyrate. GBA has the following structural formula:

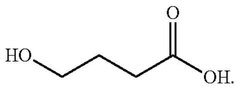

Salt forms of GHB are disclosed in U.S. Pat. Nos. 8,591,922; 8,901,173; 9,132,107; 9,555,017; and 10,195,168, which are hereby incorporated by reference in their entireties for all purposes.

The terms "effective amount" and "therapeutically effective amount" are used interchangeably in this disclosure and refer to an amount of a compound, or a salt thereof, that, when administered to a patient, is capable of performing the intended result. For example, an effective amount of a mixed salt oxybate is that amount which is required to reduce cataplexy in a patient. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The term "equivalent" when comparing Na·GHB and mixed salts forms contains the same amount of GHB within about 5% (by weight %). In preferred embodiments, a liquid formulation of a mixed salt is equivalent to the Na·GHB-containing liquid formulation Xyrem (which contains 0.409 g/mL of GHB).

In preferred embodiments, a liquid formulation of a mixed salt contains 0.234 g/mL of calcium oxybate, 0.130 g/mL of potassium oxybate, 0.096 g/mL of magnesium oxybate, and 0.040 g/mL of sodium oxybate.

As used herein, the term "patient" refers to a mammal, particularly a human.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "carrier" encompasses solvents, dispersion media, coatings, antibacterial and antifungal agents, isotonic and absorption delaying agents and the like. The use of carriers for active pharmaceutical ingredients is well known in the art. Insofar as any conventional media or agent is incompatible with the active ingredient, its use in the therapeutic compositions is not appropriate.

The term "therapeutic effect" as used herein refers to a desired or beneficial effect provided by the method and/or the composition. For example, the method for treating IH provides a therapeutic effect when the method reduces at least one symptom of IH, such as excessive daytime sleepiness, difficulty waking after sleep or cognitive dysfunction.

The term "treating" as used herein with regard to a patient, refers to improving at least one symptom of the patient's disorder. Treating can be curing, improving, or at least partially ameliorating a disorder.

The terms "substitute", "switch", "change", "transition" and "exchange" are used interchangeably in the context of the present disclosure.

The term "salt" or "salts," as used herein, refers to a compound formed by the interaction of an acid and a base, the hydrogen atoms of the acid being replaced by the positive ion or cation of the base. Pharmaceutically acceptable salts include inorganic acids such as, for example, hydrochloric or phosphoric acids, or such organic acids as malic, acetic, oxalic, tartaric, mandelic, and the like. Salts formed can also be derived from inorganic bases such as, for example, sodium, potassium, silicates, ammonium, calcium, or ferric hydroxides, and such organic bases as isopropylamine, trimethylamine, histidine, procaine and the like. In certain preferred embodiments, the salt is formed from an inorganic base that is a metal, for example, an alkali metal, such as lithium, potassium, sodium, or the like, an alkaline earth metal, such as magnesium, calcium, barium, or the like, or aluminum or zinc. Other salts may comprise ammonium. Alkali metals, such as lithium, potassium, sodium, and the like, may be used, preferably with an acid to form a pH adjusting agent. Examples of pharmaceutically acceptable base addition salts include those derived from inorganic bases like sodium hydroxide, potassium hydroxide, magnesium hydroxide, calcium hydroxide, or ammonium hydroxide, and the like (See, e.g., Berge et al., 1977, J. Pharm. Sci. 66: 1, U.S. Pat. Nos. 6,472,431 and 8,591,922).

As used herein, the terms "salt of GHB" or "salts of GHB," as used herein, refer to a compound formed by the interaction of gamma-hydroxybutyric acid (the conjugate acid of GHB) with a base, for example, NaOH, KOH, $Mg(OH)_2$, and $Ca(OH)_2$, and the like, the hydrogen atoms of the acid being replaced by the positive ion or cation of the base. Such salts may include, for example, sodium oxybate ("Na·GHB"), potassium oxybate ("K·GHB"), magnesium oxybate ("$Mg\cdot(GHB)_2$"), and calcium oxybate ("$Ca\cdot(GHB)_2$"), and the like. It will be understood by those skilled in the art that such salts may be in solid form, or such salts may be in partially or fully solvated form, for example, as when dissolved in an aqueous medium. It will be further understood by those skilled in the art, that, depending on the solubility of the salt in the aqueous medium, that the salt may be present in the aqueous medium as solvated cation(s) and anion(s), or as a precipitated solid.

The term "oxybate dosing strength" refers to the amount of GHB in a particular dose (e.g., each mL of Xyrem contains 0.5 g of sodium oxybate, which is equivalent to a 0.409 g/mL oxybate dosing strength). Although throughout the present disclosure, the oxybate dosing strength in a composition is generally expressed in terms of the amount of oxybate present in a composition, the present disclosure contemplates embodiments where the oxybate dosing strength is expressed in the Equivalent Concentration of GBA that is contained in the dose.

The Equivalent Concentration of GBA in a compositions may be calculated by the following formula:

$$\text{Equivalent Concentration of } GBA = \frac{\text{Concentration of } GHB \text{ in}(\text{g/mL}) \times 104.1\left(\text{Formula Weight of } GBA, \frac{\text{g}}{\text{mol}}\right)}{103.1\ (\text{Formula Weight of } GHB\left(\frac{\text{g}}{\text{mol}}\right)}$$

Thus, each mL of Xyrem contains 0.5 g of sodium oxybate, which is equivalent to an Equivalent Concentration of GBA of 0.413 g/mL.

The term "JZP-258" as used herein refers to a solution containing the mixed salt oxybate comprising about 8% sodium oxybate, about 23% potassium oxybate, about 21% magnesium oxybate and about 48% calcium oxybate (% mol. equiv. of GHB) and having a GHB concentration of 0.409 g/mL (or, expressed another way, an Equivalent Concentration of GBA of 0.413 g/mL). The following table describes the % mol. equiv., wt/vol %, and absolute amount of sodium oxybate, potassium oxybate, magnesium oxybate and calcium oxybate in representative doses of JZP-258.

| | % mol equivalent | wt/wt % | Amount in 1 g JZP-258 | Amount in 9 g JZP-258 |
|---|---|---|---|---|
| Na. GHB | 8 | 8 | 80 mg | 720 mg |
| K. GHB | 23 | 25.5 | 255 mg | 2,295 mg |
| Mg. $(GHB)_2$ | 21 | 19.5 | 195 mg | 1,755 mg |
| Ca. $(GHB)_2$ | 48 | 47 | 470 mg | 4,230 mg |

The term "mixed salts" or "mixed salt oxybate," as used herein, refers to salts of GHB where two, three, four or more different cations are present in combination with each other in a composition. Such mixtures of salts may include, for example, salts selected from the group consisting of Na·GHB, K·GHB, $Mg\cdot(GHB)_2$, and $Ca\cdot(GHB)_2$. Mixed salt oxybates are described in U.S. Pat. Nos. 8,591,922; 8,901,173; 9,132,107; 9,555,017; and 10,195,168, the contents of which is hereby incorporated by reference it entirety for all purposes.

The term "wt/wt %," are used herein, refers to the normalized weight percent of a particular salt in a salt mixture.

The term "wt/wt % ratio," as used herein, refers to the ratio of wt/wt % values in a mixture of salt. For example, where the salts Na·GHB, K·GHB, $Mg\cdot(GHB)_2$, and $Ca\cdot(GHB)_2$ are present in a wt/wt s's of 8%, 25.5%, 19.5% and 47%, respectively, the wt/wt % ratio of Na·GHB, K·GHB, $Mg\cdot(GHB)_2$, and $Ca\cdot(GHB)_2$ in the mixture is 8%:25.5%:19.5%:47%.

The term, "formulation," as used herein, refers to a stable and pharmaceutically acceptable preparation of a pharmaceutical composition disclosed herein.

The term, “liquid formulation,” as used herein, refers to a water-based formulation, in particular, a formulation that is an aqueous solution.

DETAILED DESCRIPTION

Idiopathic Hypersomnia

Idiopathic hypersomnia (IH) is a rare disorder of central hypersomnolence characterized by severe excessive daytime sleepiness (EDS) occurring almost daily for at least 3 months, despite normal quality, quantity, and timing of nocturnal sleep (American Academy of Sleep Medicine International Classification of Sleep Disorders, Third Edition [AASM 2014]). The pathophysiology of idiopathic hypersomnia remains to be elucidated. The clinical phenotype of IH is heterogeneous based on presence or absence of ancillary symptoms, most notably of which include prolonged sleep time and sleep inertia (Basetti and Aldrich (1997), Idiopathic hypersomnia. A series of 42 patients, *Brain: A Journal of Neurology,* 120(8), 1423-35 [Basetti and Aldrich 1997]; Anderson et al. (2007), Idiopathic hypersomnia: a study of 77 cases, *Sleep,* 30(10), 1274-81 [Anderson 2007]; Ali et al. (2009), Idiopathic hypersomnia: clinical features and response to treatment, *Journal of Clinical Sleep Medicine,* 5(6), 562-68 [Ali 2009]; Ahmed et al. (2016), Overview of Central Disorders of Hypersomnolence, *Reference Module in Neuroscience and Biobehavioral Psychology*; Evangelista et al. (2018), Update on treatment for idiopathic hypersomnia, *Expert Opinion on Investigational Drugs,* 27(2), 187-92 [Evangelista 2018]; Leu-Semenescu et al. (2016), Benefits and risk of sodium oxybate in idiopathic hypersomnia versus narcolepsy type 1: a chart review, *Sleep Medicine,* 17, 38-44 [Leu-Semenescu 2016]). Nocturnal sleep time and 24-hour sleep time are often prolonged (e.g., ≥11 hours) in patients with IH, and can be used to confirm the diagnosis (AASM 2014). Sleep inertia or “sleep drunkenness” defined as “prolonged difficulty waking up with repeated returns to sleep, irritability, automatic behavior, and confusion” is reported in 36 to 66% of patients (AASM 2014; Vernet et al. (2010), Subjective symptoms in idiopathic hypersomnia: beyond excessive sleepiness, *Journal of Sleep Research,* 19(4), 525-34; Roth et al. (1972), Hypersomnia with sleep drunkenness, *Archives of General Psychiatry,* 26(5), 456-62). The sleep inertia experienced by patients with IH represents a clinical challenge because it is difficult for some patients to awaken enough to take their stimulant medication (Trotti L M (2017), Idiopathic Hypersomnia, *Sleep Medicine Clinics* 12(3), 331-44 [Trotti 2017]). Other less specific features of IH include sleep paralysis and sleep hallucinations (hypnagogic or hypnopompic hallucinations occurring at the transition from wake to sleep or sleep to wake), which are present in approximately 20 and 25% of patients, respectively (Khan and Trotti (2015), Central disorders of hypersomnolence, *Chest,* 148(1), 262-73 [Khan and Trotti 2015]). The majority of patients with IH have symptoms that remain stable over many years and require long term treatment, but spontaneous remission is seen in a minority of patients with IH (11-33%) within up to 5.5 years after diagnosis (Anderson 2007; Basetti and Aldrich 1997; Kim et al. (2016), Different fates of excessive daytime sleepiness: survival analysis for remission, *Acta Neurologica Scandinavica,* 134(1), 35-41).

Idiopathic hypersomnia is one of three central disorders of persistent hypersomnolence not associated with another illness or substance; narcolepsy type 1 and narcolepsy type 2 comprise the other two (AASM 2014). Features that distinguish IH from narcolepsy type 1 include the absence of cataplexy and normal levels of hypocretin according to the ICSD-3 and a review by Billiard M (2017), Epidemiology of central disorders of hypersomnolence, *Reference Module in Neuroscience and Biobehavioral Psychology* [Billiard 2017]. Distinguishing IH from narcolepsy type 2 is more challenging, as clinical features can be very similar. The diagnostic criteria for IH and narcolepsy type 2 overlap with respect to irrepressible need to sleep or daytime lapses into sleep and the absence of cataplexy. The diagnostic criteria for narcolepsy type 2 and IH differ with respect to findings on sleep diagnostic testing. The diagnostic criteria for narcolepsy type 2 require either a sleep onset rapid eye movement period (SOREMP) on Polysomnography (PSG) or ≥2 SOREMPs on multiple sleep latency test (MSLT), and a mean sleep latency ≤8 minutes on MSLT; the diagnostic criteria for IH require the absence of a SOREMP on PSG and ≤1 SOREMP on MSLT, and either a mean sleep latency ≤8 minutes on MSLT or total 24-hour sleep time ≥660 minutes (Billiard 2017, AASM 2014). Idiopathic hypersomnia is a diagnosis of exclusion, and it is important that physicians rule out other conditions that can cause hypersomnolence (e.g. sleep apnea, narcolepsy, circadian rhythm disorders, sleep deprivation, medical and psychiatric disorders) (Khan and Trotti 2015).

For more information about IH, see the following references which are hereby incorporated by reference in their entireties: Lopez et al. (2017), French consensus. Management of patients with hypersomnia: Which strategy?, *Revue Neurologique,* 173(1), 8-18; Pizza et al. (2013), Polysomnographic study of nocturnal sleep in idiopathic hypersomnia without long sleep time, *Journal of Sleep Research,* 22(2), 185-96; Billiard and Sonka (2016), Idiopathic hypersomnia, *Sleep Medicine Reviews,* 29, 23-33; Delrosso et al. (2014), Manual Characterization of Sleep Spindle Index in Patients with Narcolepsy and Idiopathic Hypersomnia, *Sleep Disorders,* 2014; Evangelista et al. (2018) Update on treatment for idiopathic hypersomnia, *Expert Opin Investig Drugs,* 27(2):187-192; Leu-Semenescu et al. (2016), Benefits and risk of sodium oxybate in idiopathic hypersomnia versus narcolepsy type 1: a chart review, *Sleep Med.,* 17:38-44; Mignot E J (2012), A practical guide to the therapy of narcolepsy and hypersomnia syndromes, *Neurotherapeutic,* 9(4), 739-52; Ali et al. (2009), Idiopathic hypersomnia: clinical features and response to treatment, *Journal of Clinical Sleep Medicine,* 5(6), 562-68.

The EDS and other symptoms experienced by patients with IH can negatively impact quality of life, ability to sustain employment, and create a safety risk when operating a motor vehicle. Compared with controls, patients with IH report increased activity limitations due to both physical capabilities and emotional problems, decreased energy, decreased social functioning, increased perception of general health problems, and increased feelings of depression and anxiety (Ozaki et al. (2008), Health-related quality of life among drug-naïve patients with narcolepsy with cataplexy, narcolepsy without cataplexy, and idiopathic hypersomnia without long sleep time, *Journal of Clinical Sleep Medicine,* 4(6), 572 [Ozaki 2008]). Patients with IH face many disorder-associated challenges that interfere with their ability to secure and sustain employment, including tardiness and absenteeism due to debilitating EDS and sleep inertia that cannot be effectively mitigated through napping, increasing sleep time, or typical strategies to awaken in the morning such as use of alarm clocks, light exposure, or routines (Philip (2001), Is there a link between subjective daytime somnolence and sickness absenteeism? A study in a working population, *J Sleep Res.* 10(2):111-5; Vernet et al.

(2010), Subjective symptoms in idiopathic hypersomnia: beyond excessive sleepiness, *Journal of Sleep Research,* 19(4), 525-34 [Vernet 2010]). In addition to the potential for absenteeism at work, performance at work may be compromised in patients with IH due to EDS and other aspects of the disorder process including altered cognition, attention deficit, and symptoms of autonomic dysfunction (faintness, difficulties in regulating body temperature, headaches and palpitations) (Oosterloo et al. (2006) Possible confusion between primary hypersomnia and adult attention-deficit/hyperactivity disorder, *Psychiatry Res.* 143(2-3):293-7; Vernet 2010). Lastly, the symptoms associated with IH can pose significant risks when operating a motor vehicle. In a large cross-sectional study of 282 patients with central disorders of hypersomnolence and 470 healthy controls, patients with central disorders of hypersomnolence reported a 2-fold increase in the prevalence of vehicular accidents in the preceding 5 years compared with controls (Pizza et al. (2015), Car Crashes and Central Disorders of Hypersomnolence: A French Study, *PLoS One.* 2015; 10(6):e0129386. Published 2015 Jun. 8). In the same study, the risk of recent vehicular accidents among patients with IH was 2.04 times that of the healthy control population. In a separate Japanese study, 50% of drug naïve patients with IH without long sleep time reported accidents or near misses within the previous 5 years (Ozaki 2008).

There are currently no approved medications for the treatment of IH. The pathophysiology is unknown, and the disorder is treated symptomatically. Few large randomized controlled trials have evaluated therapies for EDS in IH, and treatment is guided by expert opinion (Khan and Trotti 2015; Saini and Rye (2017), Hypersomnia: evaluation, treatment, and social and economic aspects, *Sleep Medicine Clinics,* 12(1), 47-60; Trotti 2017; Evangelista 2018). Thus, despite somewhat different clinical features in patients with IH and narcolepsy, the same medications and treatment approaches that are used to treat narcolepsy are recommended off-label for the management of EDS in IH (Evangelista 2018, Morgenthaler et al. (2007), Practice Parameters for the Treatment of Narcolepsy and other Hypersomnias of Central Origin An American Academy of Sleep Medicine Report, *Sleep,* 30(12), 1705-1711. These include wake-promoting agents and traditional stimulants such as modafinil and armodafinil (Lavault et al. (2011), Benefit and risk of modafinil in idiopathic hypersomnia vs. narcolepsy with cataplexy, *Sleep Medicine,* 12(6), 550-56; Anderson 2007), amphetamine, and methylphenidate (Anderson 2007). Other agents that have been used or tested in clinical trials in patients with IH include sodium oxybate (Leu-Semenescu 2016), pitolisant (Leu-Semenescu et al., (2014), Effects of pitolisant, a histamine H3 inverse agonist, in drug-resistant idiopathic and symptomatic hypersomnia: a chart review, *Sleep Med.* 15(6):681-7), clarithromycin (Trotti et al. (2014), Improvement in daytime sleepiness with clarithromycin in patients with GABA-related hypersomnia: Clinical experience, *J Psychopharmacol.* 28(7): 697-702), flumazenil (Trotti et al. (2016), Flumazenil for the Treatment of Refractory Hypersomnolence: Clinical Experience with 153 Patients, *Journal of clinical sleep medicine,* 12(10) 1389-1394), levothyroxine (Shinno et al. (2009), Successful treatment with levothyroxine for idiopathic hypersomnia patients with subclinical hypothyroidism, *General Hospital Psychiatry,* 31(2), 190-93), mazindol (Nittur et al. (2013), Mazindol in narcolepsy and idiopathic and symptomatic hypersomnia refractory to stimulants: a long-term chart review, *Sleep Medicine,* 14(1), 30-36), and pentetrazol (Clinicaltrials.gov NCT02512588).

Oxybate

Sodium oxybate (Na·GHB), commercially sold as Xyrem®, is approved for the treatment of cataplexy or excessive daytime sleepiness in patients 7 years of age or older with narcolepsy. Administration of the approved daily dose of Xyrem® (6-9 grams per night administered orally) results in the patient ingesting from 1100-1638 mg of sodium daily. The American Heart Association has recommended a daily sodium intake of less than 2300 mg and an "ideal" daily intake of <1500 mg (AHA 2017 (https://www.heart.org/-/media/data-import/downloadables/8/2/0/pe-abh-why-should-i-limit-sodium-ucm_300625.pdf); Whelton et al. (2012), Sodium, blood pressure, and cardiovascular disorder: further evidence supporting the American Heart Association sodium reduction recommendations, Circulation, 126(24):2880-9) and a recent report from The National Academies of Science, Engineering, and Medicine (2019) advises adults to "reduce intake if above 2300 mg/day" based on strong causal evidence of cardiovascular disorder risk above this level. Thus, Xyrem® administration provides a sodium intake that makes up a substantial amount of the recommended daily intake goals, which renders adherence to daily sodium intake goals challenging since—even without the consideration of Xyrem—the average daily sodium intake for Americans ≥2 years of age is ≥3400 mg (US Department of Agriculture, Agricultural Research Service. Nutrient intakes from food: mean amounts consumed per individual, by gender and age, in the United States, 2009-2010. In: What We Eat in America, NHANES 2009-2010. Washington, DC: US Department of Agriculture, Agricultural Research Service; 2012).

Mixed Salt Oxybate

JZP-258 (a preferred embodiment of the present disclosure) was developed to provide the same treatment benefits as Xyrem with substantially less sodium.

JZP-258 is a mixed salt oxybate that contains calcium oxybate, magnesium oxybate, potassium oxybate, and sodium oxybate, and it provides 87-131 mg of sodium when administered in the dose range of 6-9 grams nightly. This amount is 92% less sodium than that provided by Xyrem® administration at an equivalent dose. Though important for every person, daily sodium intake goals are a vital consideration for all patients with the lifelong disorder of narcolepsy, given the increased presence of multiple cardiovascular comorbidities, including hypertension, congestive heart failure, and myocardial infarction (Jennum et al. (2013), Comorbidity and mortality of narcolepsy: a controlled retro- and prospective national study. *Sleep,* 36(6), 835-40; Ohayon M M (2013), Narcolepsy is complicated by high medical and psychiatric comorbidities: a comparison with the general population, *Sleep Medicine,* 14(6), 488-92; and Black et al. (2017), Medical comorbidity in narcolepsy: findings from the Burden of Narcolepsy Disease (BOND) study, *Sleep Medicine,* 33, 13-18).

The following patents, publications and application are related to the present disclosure and are hereby incorporated by reference in their entireties for all purposes: U.S. Pat. Nos. 6,472,431; 6,780,889; 7,262,219; 8,263,650; 8,461,203; 8,859,619; 9,539,330; 7,851,506; 8,324,275; 8,952,062; 8,731,963; 8,772,306; 8,952,029; 9,050,302; 9,486,426; 10,213,400; 8,591,922; 8,901,173; 9,132,107; 9,555,017; 10,195,168; 8,778,301; 9,801,852; 8,771,735; 8,778,398; 9,795,567; U.S. Patent Publication Nos. US 2018/0042855, and U.S. application Ser. Nos. 16/688,797, 62/769,380 and 62/769,382.

In some embodiments, the methods of the present disclosure comprise administering sodium oxybate or a mixed salt oxybate to a patient in need thereof (such as a patient with IH). In some embodiments, the mixed salt oxybate comprises gamma-hydroxybutyrate (GHB) and three or four or more pharmaceutically acceptable cations of an alkali metal or an alkaline earth metal. In some embodiments, the mixed salt oxybate comprises GHB and more than one pharmaceutically acceptable cations of an alkali metal or an alkaline earth metal.

In some embodiments, the mixed salt oxybate comprises GHB and two, three, or four cations selected from the group consisting of $Na^+$, $K^+$, $Mg^{+2}$, and $Ca^{+2}$. In some embodiments, mixed salt oxybate comprises GHB and all three cations selected from the group consisting of $K^+$, $Mg^{+2}$, and $Ca^{+2}$. In some embodiments, the mixed salt oxybate does not contain Na+, or comprises less than 100% of $Na^+$.

In some embodiments, the mixed salt oxybate comprises two, three, or four salts selected from the group consisting of a sodium salt of hydroxybutyrate (Na·GHB), a potassium salt of gamma-hydroxybutyrate (K·GHB), a magnesium salt of gamma-hydroxybutyrate ($Mg\cdot(GHB)_2$), and a calcium salt of gamma-hydroxybutyrate ($Ca\cdot(GHB)_2$). In some embodiments, the mixed salt oxybate comprises varying weight/weight percentages (wt/wt %) of Na·GHB, K·GHB, $Mg\cdot(GHB)_2$, and $Ca\cdot(GHB)_2$.

In some embodiments, any of the salts, such as the Na·GHB salt, the K·GHB salt, the $Mg\cdot(GHB)_2$ salt or the $Ca\cdot(GHB)_2$, is present in about 1%-5%, about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, about 90%-95%, or about 95%-100% (wt/wt %). In some embodiments, the Na·GHB salt is present in a wt/wt % of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (wt/wt %). In some embodiments, the Na·GHB salt is absent.

In some embodiments, where the mixed salt oxybate comprises a mixture of Na·GHB, K·GHB, $Mg\cdot(GHB)_2$, and $Ca\cdot(GHB)_2$, the Na·GHB salt is present in a wt/wt % of about 1%-15%, 5%-10%, or about 8%; the K·GHB salt is present in a wt/wt % of about 10%-30%, 15%-25%, or about 25.5%; the $Mg\cdot(GHB)_2$ salt is present in a wt/wt % of about 10%-30%, 15%-25%, or about 19.5%; and the $Ca\cdot(GHB)_2$ salt is present in a wt/wt % of about 30%-60%, 40%-50, or about 47% (wt/wt %).

In some embodiments, the mixed salt oxybate comprises about 8% of sodium oxybate (wt/wt %), about 25.5% of potassium oxybate (wt/wt %), about 19.5% of magnesium oxybate (wt/wt %) and about 47% of calcium oxybate (wt/wt %). In some embodiments, where the mixed salt oxybate comprises a mixture of Na·GHB, K·GHB, $Mg\cdot(GHB)_2$, and $Ca\cdot(GHB)_2$, the Na·GHB, K·GHB, $Mg\cdot(GHB)_2$, and $Ca\cdot(GHB)_2$ salts are present in a wt/wt % ratio of about 8:25.5:19.5:47, respectively.

In some embodiments, a mixed salt oxybate of the present disclosure is dissolved in a liquid (such as water) to provide a pharmaceutical composition and the concentration of the mixed salt oxybate is expressed in terms of the wt/vol %. In some embodiments, where the mixed salt oxybate comprises a mixture of Na·GHB, K·GHB, $Mg\cdot(GHB)_2$, and $Ca\cdot(GHB)_2$, the Na·GHB salt is present in a wt/vol % of about 1%-15%, 5%-10%, or about 8%; the K·GHB salt is present in a wt/vol % of about 10%-30%, 15%-25%, or about 26%; the $Mg\cdot(GHB)_2$ salt is present in a wt/vol % of about 10%-30%, 15%-25%, or about 19.2%; and the $Ca\cdot(GHB)_2$ salt is present in a wt/vol % of about 30%-60%, 40%-50, or about 46.8% (wt/vol %).

In some embodiments, the liquid pharmaceutical composition containing the mixed salt oxybate comprises about 8% of sodium oxybate (wt/vol %), about 26.0% of potassium oxybate (wt/vol %), about 19.2% of magnesium oxybate (wt/vol %) and about 46.8% of calcium oxybate (wt/vol %).

In some embodiments, the mixed salt oxybate comprises varying percentages of oxybate, expressed as % molar equivalents (% mol. equiv.) of Na·GHB, K·GHB, $Mg\cdot(GHB)_2$, and $Ca\cdot(GHB)_2$. The terms "% molar equivalents" and "% mol. equiv.," as used herein, refer to molar composition of salts expressed as a percent of GHB equivalents. Those skilled in the art will understand that as each GHB unit is considered to be one molar equivalent, the monovalent cations, $Na^+$ and $K^+$, have one molar equivalent per salt, and the divalent cations, $Mg^{+2}$ and $Ca^{+2}$, have two molar equivalents per salt. See U.S. Pat. Nos. 8,591,922; 8,901,173; 9,132,107; 9,555,017; 10,195,168 for amounts of % mol. equiv. useful in the present disclosure.

In some embodiments, any of the salts, such as the Na·GHB salt, the K·GHB salt, the $Mg\cdot(GHB)_2$ salt or the $Ca\cdot(GHB)_2$, is present in about 1%-5%, about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, about 90%-95%, or about 95%-100% (% mol. equiv.). In some embodiments, the Na·GHB salt is present in a % mol. equiv. of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (% mol. equiv.). In some embodiments, the Na·GHB salt is absent.

In some embodiments, where the mixed salt oxybate comprises a mixture of Na·GHB, K·GHB, $Mg\cdot(GHB)_2$, and $Ca\cdot(GHB)_2$, the Na·GHB salt is present in a % mol. equiv. of about 1%-15%, 5%-10%, or about 8%; the K·GHB salt is present in a % mol. equiv. of about 10%-30%, 15%-25%, or about 23%; the $Mg\cdot(GHB)_2$ salt is present in a % mol. equiv. of about 10%-30%, 15%-25%, or about 21%; and the $Ca\cdot(GHB)_2$ salt is present in a % mol. equiv. of about 30%-60%, 40%-50, or about 48% (% mol. equiv.).

In some embodiments, the mixed salt oxybate comprises about 8% mol. equiv. of sodium oxybate, about 23% mol. equiv. of potassium oxybate, about 21% mol. equiv. of magnesium oxybate and about 48% mol. equiv. of calcium oxybate. In some embodiments, where the mixed salt oxybate comprises a mixture of Na·GHB, K·GHB, $Mg\cdot(GHB)_2$, and $Ca\cdot(GHB)_2$, wherein the mixture comprises Na·GHB, K·GHB, $Mg\cdot(GHB)_2$, and $Ca\cdot(GHB)_2$ salts are present in a % mol. equiv. ratio of about 8:23:21:48, respectively.

In some embodiments, where the pharmaceutical composition comprises a mixture of Na·GHB, K·GHB, and $Ca\cdot(GHB)_2$, the Na·GHB salt is present in a % mol. equiv. of about 5%-40%, the K·GHB salt is present in a % mol. equiv. of about 10%-40%, and the $Ca\cdot(GHB)_2$ salt is present in a % mol. equiv. of about 20%-80%.

Pharmaceutical Compositions:

In some embodiments, the mixed salt oxybate is in the form of a pharmaceutical composition that is suitable for administration in the methods of the present disclosure. In some embodiments, the pharmaceutical composition comprises an aqueous solution. Other formulations can be solid formulations.

In some embodiments, the sodium oxybate is in the form of a pharmaceutical composition that is suitable for administration in the methods of the present disclosure. In some embodiments, the pharmaceutical composition comprises an aqueous solution. Other formulations can be solid formulations.

In some embodiments, the concentration of the mixture of salts of GHB in the liquid solution is about 50 mg/mL-950 mg/mL, about 250 mg/mL-750 mg/mL, about 350 mg/mL-650 mg/mL, or about 450 mg/mL-550 mg/mL. In some embodiments, the concentration of the mixture of salts of GHB in the solution is about 500 mg/mL. In some embodiments, the pH of the pharmaceutical composition is about 7.0-9.0, about 7.0-8.5, or about 7.3-8.5.

In some embodiments, the pharmaceutical composition is chemically stable and resistant to microbial growth. In some embodiments, the pharmaceutical composition does not need, and is free of preservatives. See U.S. Pat. Nos. 6,472,431; 6,780,889; 7,262,219; 8,263,650; 8,461,203 and others for a relationship between pH and GHB concentration and their effect on microbial growth.

In some embodiments, a pH adjusting or buffering agent may be added to the pharmaceutical composition. The choice of a pH adjusting or buffering agent may affect the resistance to microbial challenge and/or the stability of GHB, as measured by the reduction in assayable GHB. Pharmaceutical compositions of GHB, pH adjusted or buffered with malic acid are resistant to both microbial growth and chemical degradation of GHB, and are preferred. Other pH adjusting or buffering agents may be selected. Agents that adjust pH that are selected on this basis will undergo a taste testing study. However, any pH adjusting or buffering agent disclosed herein or as would be known to those skilled in the art is contemplated as being useful from the compositions or formulations disclosed herein. Of course, any salt, flavoring agent, excipient, or other pharmaceutically acceptable addition described herein or as would be known to those skilled in the art is contemplated as being useful for the compositions or formulations disclosed herein.

In some embodiments, the pH adjusting or buffering agent is an acid. In some embodiments, the pH adjusting or buffering agent is an inorganic acid or an organic acid. In some embodiments, the pH adjusting or buffering agent is selected from the group consisting of malic acid, citric acid, acetic acid, boric acid, lactic acid, hydrochloric acid, phosphoric acid, sulfuric acid, sulfonic acid, and nitric acid. In some embodiments, the pH adjusting or buffering agent is malic acid. See U.S. Pat. No. 6,472,431.

The aqueous solutions disclosed herein typically comprise an effective amount of GHB, which may be dissolved or dispersed in a pharmaceutically acceptable carrier and/or an aqueous medium.

Formulations

In some embodiments, the pharmaceutical compositions disclosed herein are provided in a formulation that is suitable for administration in the methods of the present disclosure.

In some embodiments, the formulation is a liquid formulation. In some embodiments, the formulation is a solid formulation. In some embodiments, the formulation is suitable for oral administration. See incorporated by reference U.S. Pat. Nos. 6,472,431; 6,780,889; 7,262,219; 8,263,650; 8,461,203, 8,859,619, 8,591,922, 8,901,173, 9,132,107, 9,539,330, 9,555,017, 9,795,567, 10,195,168, U.S. Ser. Nos. 16/688,797, 62/769,380 and 62/769,382 and U.S. Patent Publication No. 2018/0263936 for example. These patents present examples of flavoring agents, sweeteners, coloring agents, surfactants, carriers, excipients, binders, buffering compounds or agents and other formulation ingredients.

In some embodiments, the formulation is chemically stable and resistant to microbial growth. In some embodiments, the formulation is free of preservatives. In some embodiments, the level of gamma-butyrolactone (GBL) is 0.1% or less of the formulation.

In preferred embodiments, the formulation is a liquid formulation, wherein the formulation comprises 0.234 g/mL of calcium oxybate, 0.130 g/mL of potassium oxybate, 0.096 g/mL of magnesium oxybate, and 0.040 g/mL of sodium oxybate (which contains 0.413 g/mL of GHB).

In some embodiments, the formulation is suitable for administration in a single or multiple dosage regimen per day. See U.S. Ser. Nos. 16/688,797, 62/769,380 and 62/769,382.

Any of the above formulations may be prepared and/or packaged as a powdered or dry form for mixing with an aqueous medium before oral administration, or they may be prepared in an aqueous medium and packaged. After mixing with an aqueous medium, preferably to prepare a solution, these formulations are resistant to both microbial growth and chemical conversion of GHB to GBL, thereby increasing the shelf-life of therapeutic formulations of GHB in an aqueous medium. These formulations then provide an easily titratable liquid medium for measuring the dosage of GHB to be administered to a patient.

The GHB may be lyophilized for more ready formulation into a desired vehicle or medium where appropriate. The active compounds may be formulated for parenteral administration, e.g., formulated for injection via intravenous, intraarterial, intramuscular, sub-cutaneous, intralesional, intraperitoneal or other parenteral routes. The preparation of a composition that comprises an aqueous solution that contains a GHB agent as an active component or ingredient will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared; and the preparations can also be emulsified. See U.S. Pat. Nos. 6,472,431; 6,780,889; 7,262,219; 8,263,650; 8,461,203, 8,591,922, 8,901,173, 9,132,107, 9,555,017, 9,795,567, 10,195,168, U.S. Ser. Nos. 16/688,797, 62/769,380 and 62/769,382, and U.S. Patent Publication No. 2018/0263936 for example for more information about parenteral administration.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For oral therapeutic administration, the active compounds may be incorporated with excipients and used in the form of tablets, buccal tablets or tabs, troches, capsules, elixirs, suspensions, syrups, wafers, and the like, to be admixed with an aqueous medium. Such compositions and preparations should contain at least 0.1% of active compound. The percentage of the compositions and preparations may, of course, be varied and may conveniently be between about 2-75% of the weight of the unit, or preferably between 25-60%. The amount of active compounds in such therapeutically useful compositions is such that a suitable dosage will be obtained. See U.S. Pat. Nos. 6,472,431; 6,780,889; 7,262,219; 8,263,650; 8,461,203, 8,591,922, 8,901,173, 9,132,107, 9,555,017, 9,795,567, 10,195,168, U.S. Ser. Nos. 16/688,797, 62/769,380 and 62/769,382, and U.S. Patent Publication No. 2018/0263936 for example.

Methods of the Present Disclosure

In one aspect, the present disclosure provides methods for treating idiopathic hypersomnia (IH) in a patient in need thereof by administering a therapeutically effective amount of sodium oxybate to the patient. In some embodiments, the sodium oxybate is used to treat a patient with IH, to treat IH, to treat the symptoms of IH, to treat excessive daytime sleepiness in a patient with IH, to treat sleep inertia in a patient with IH and to achieve adequate sleep duration in a patient with IH.

In one aspect, the present disclosure provides methods for treating idiopathic hypersomnia (IH) in a patient in need thereof by administering a therapeutically effective amount of a mixed salt oxybate to the patient. In some embodiments, the mixed salt oxybate is used to treat a patient with IH, to treat IH, to treat the symptoms of IH, to treat excessive daytime sleepiness in a patient with IH, to treat sleep inertia in a patient with IH and to achieve adequate sleep duration in a patient with IH.

Throughout the present disclosure, the doses of oxybate are generally expressed in terms of the amount of a mixed salt oxybate (such as JZP-258). However, the present disclosure contemplates embodiments where the oxybate dose recited for the mixed salt oxybate refers to amount of sodium oxybate (e.g., where "about 5 g of mixed salt oxybate" is disclosed, embodiments of "about 5 g of sodium oxybate" are contemplated by the present disclosure). Similarly, throughout the present disclosure, the amounts of oxybate administered in the methods of the present disclosure are generally expressed in terms of the amount of a mixed salt oxybate (such as JZP-258) administered. However, the present disclosure also contemplates embodiments where the administered oxybate dose recited for the mixed salt oxybate refers to amount of sodium oxybate administered (e.g., where administration of "about 5 g of mixed salt oxybate" is disclosed, embodiments of administration of "about 5 g of sodium oxybate" are contemplated by the present disclosure).

The present disclosure provides methods of treating a patient with IH. Methods of diagnosing a patient with IH are known to those skilled in the art. In some embodiments, a patient is diagnosed with IH using the criteria set forth in International Classification of Sleep Disorders third edition (ICSD-3). In some embodiments, a patient is diagnosed with IH using the criteria set forth in a prior version of the International Classification of Sleep Disorders (e.g., International Classification of Sleep Disorders: Diagnostic and Coding Manual, second edition (ICSD-2)). In some embodiments, a patient is diagnosed with IH using the criteria set forth in the Diagnostic and Statistical Manual of Mental Disorders—fifth edition (DSM-5). In some embodiments, a patient is diagnosed with IH using the criteria set forth in a prior version of the Diagnostic and Statistical Manual of Mental Disorders.

According to the methods of the present disclosure, the mixed salt oxybate that is administered may be any of the mixed salt oxybate compositions described herein. In some embodiments, the relative amount of each salt in the mixed salt oxybate that is administered is expressed in terms of wt/wt %. In some embodiments, the mixed salt oxybate comprises sodium oxybate, potassium oxybate, magnesium oxybate and calcium oxybate, and wherein the mixed salt oxybate comprises about 5%-40% of sodium oxybate (wt/wt %). In some embodiments, the mixed salt oxybate comprises about 5%-40% of sodium oxybate (wt/wt %), about 10%-40% of potassium oxybate (wt/wt %), about 5%-30% of magnesium oxybate (wt/wt %), and about 20%-80% of calcium oxybate (wt/wt %). In some embodiments, the mixed salt oxybate comprises about 8% of sodium oxybate (wt/wt %), about 25.5% of potassium oxybate (wt/wt %), about 19.5% of magnesium oxybate (wt/wt %) and about 47% of calcium oxybate (wt/wt %).

In some embodiments, the relative amount of each salt in the mixed salt oxybate that is administered in a liquid pharmaceutical composition is expressed in terms of wt/vol %. In some embodiments, the liquid pharmaceutical composition comprises a mixed salt oxybate comprising sodium oxybate, potassium oxybate, magnesium oxybate and calcium oxybate, and wherein the mixed salt oxybate comprises about 5%-40% of sodium oxybate (wt/vol %). In some embodiments, the liquid pharmaceutical composition comprises a mixed salt oxybate comprising about 5%-40% of sodium oxybate (wt/vol %), about 10%-40% of potassium oxybate (wt/vol %), about 5%-30% of magnesium oxybate (wt/vol %), and about 20%-80% of calcium oxybate (wt/vol %). In some embodiments, the liquid pharmaceutical composition comprises the mixed salt oxybate comprising about 8% of sodium oxybate (wt/vol %), about 26% of potassium oxybate (wt/vol %), about 19.2% of magnesium oxybate (wt/vol %) and about 46.8% of calcium oxybate (wt/vol %).

In some embodiments, the relative amount of each salt in the mixed salt oxybate that is administered is expressed in terms of % mol. equiv. In some embodiments, the mixed salt oxybate comprises sodium oxybate, potassium oxybate, magnesium oxybate and calcium oxybate, and wherein the mixed salt oxybate comprises about 5%-40% mol. equiv. of sodium oxybate. In some embodiments, the mixed salt oxybate comprises about 5%-40% mol. equiv. of sodium oxybate, about 10%-40% mol. equiv. of potassium oxybate, about 5%-30% mol. equiv. of magnesium oxybate, and about 20%-80% mol. equiv. of calcium oxybate. In some embodiments, the mixed salt oxybate comprises about 8% mol. equiv. of sodium oxybate, about 23% mol. equiv. of potassium oxybate, about 21% mol. equiv. of magnesium oxybate and about 48% mol. equiv. of calcium oxybate.

In some embodiments, a therapeutically effective dose is achieved by starting the patient on an initial daily dose and titrating to an efficacious and tolerated dose by gradually increasing or decreasing the daily administered amount of mixed salt oxybate until a dose that is effective (i.e., the patient with IH is treated) and tolerated is achieved. In some embodiments, the efficacious dose is a dose that improves the patient's excessive daytime sleepiness (EDS) as measured by a decrease in the patient's Epworth Sleepiness Scale (ESS) Score compared to baseline prior to the treatment. In some embodiments, the efficacious dose improves the EDS as measured by a decrease in the patient's ESS of at least 1, 2, 3, 4, 5, or 6 compared to baseline prior to the treatment. In some embodiments, the efficacious dose is a dose that provides an ESS of less than 11 in the treated patient.

In some embodiments, the efficacious dose is a dose that improves at least one symptom of the patient's IH as measured by an improvement in the patient's Idiopathic Hypersomnia Severity Scale (IHSS) Score compared to baseline prior to the treatment. In some embodiments, the efficacious dose is a dose that provides an IHSS score of less than 22 in the treated patient.

In some embodiments, the efficacious dose is a dose that improves at least one symptom of the patient's IH as measured by an improvement in the patient's Patient Global Impression of change (PGIc), Clinical Global Impression of change (CGIc), Functional Outcomes of Sleep Questionnaire, short version (FOSQ-10), Visual analog scale (VAS) for sleep inertia, Total sleep time (TST) from daily sleep diary, or Work Productivity and Activity Impairment Questionnaire: Specific Health Problem (WPAI:SHP) compared to baseline prior to the treatment. In some embodiments, the present disclosure provides methods for switching a patient with IH who is currently being administered sodium oxybate to a therapeutically effective dose of a mixed salt oxybate. In some embodiments, the switching comprises administering a mixed salt oxybate to a patient with IH and is being treated with sodium oxybate, wherein the dose amount and schedule of the sodium oxybate and the mixed salt oxybate are the same. For example, a patient who is treated once a day with 0.5 g of sodium oxybate is switched to a once a day dose of 0.5 g of a mixed salt oxybate. In some further embodiments, after switching the patient from sodium oxybate to a mixed salt oxybate, the method comprises titrating to an efficacious and tolerated dose by gradually increasing or decreasing the daily administered amount of mixed salt oxybate until a dose that is effective and tolerated is achieved.

In some embodiments, after switching a patient from sodium oxybate to a mixed salt oxybate composition, the mixed salt oxybate composition is administered with food. In some embodiments, after switching a patient from sodium oxybate to a mixed salt oxybate composition, the mixed salt oxybate composition is administered without food. In some embodiments, after switching a patient from sodium oxybate to a mixed salt oxybate composition, the mixed salt oxybate composition is administered with or without regard to food. In some embodiments, the patient is administered the mixed salt oxybate composition at least 2 h after the patient's last meal. In some embodiments, the patient is administered their first dose of the mixed salt oxybate composition (i.e., the dose where the patient transitions from sodium oxybate to the mixed salt oxybate composition) at least 2 h after the patient's last meal. In some embodiments, the patient is administered their first dose of the mixed salt oxybate composition at least 2 h, at least 1.5 h, about 1.0 h, about 0.5 h or about 15 min after the patient's last meal. In some embodiments, the mixed salt oxybate is administered with or without regard to food after the titration period as described herein (i.e., when a stable dose of the mixed salt oxybate composition is achieved).

In some embodiments, the present disclosure provides methods for treating idiopathic hypersomnia in a patient in need thereof, the method comprising administering a therapeutically effective amount of a mixed salt oxybate to a patient who is not being administered sodium oxybate for the treatment of idiopathic hypersomnia (i.e. sodium oxybate naïve). In some embodiments, the patient is not being treated with sodium oxybate when treatment with the mixed salt oxybate is initiated. In some embodiments, the patient has not been administered sodium oxybate for at least about 2 weeks prior to treatment with the mixed salt oxybate. In some embodiments, the patient has not been administered sodium oxybate for at least about 14 to 30 days prior to treatment with the mixed salt oxybate. In some embodiments, the patient has never been previously administered with sodium oxybate prior to treatment with the mixed salt oxybate.

In some embodiments, the sodium oxybate naïve patient is administered an initial dose of the mixed oxybate (e.g., once or twice daily). In some further embodiments, after administering an initial daily dose of the mixed salt oxybate to the patient, the method comprises titrating to an efficacious and tolerated dose by gradually increasing the daily administered amount of mixed salt oxybate until a dose that is effective and tolerated is achieved.

In Some Embodiments, the Methods of the Present Disclosure Comprise:

(a) administering an initial daily dose of the mixed salt oxybate to the patient and (b) titrating the dose to provide a therapeutically effective amount of the mixed salt oxybate.

In Some Embodiments, the Methods of the Present Disclosure Comprise:

(a) administering an initial daily dose of the mixed salt oxybate to a sodium oxybate naïve patient, and (b) titrating the dose to provide a therapeutically effective amount of the mixed salt oxybate.

In some embodiments, the initial daily dose is from about 0.5 g to about 4.5 g of the mixed salt oxybate. In some embodiments, the initial daily dose is less than about 4.5 g of the mixed salt oxybate. In some embodiments, the initial daily dose is about 0.25 g of the mixed salt oxybate. In some embodiments, the initial daily dose is about 0.50 g of the mixed salt oxybate. In some embodiments, the initial daily dose is about 1.0 g of the mixed salt oxybate. In some embodiments, the initial daily dose is about 1.5 g of the mixed salt oxybate. In some embodiments, the initial daily dose is about 2.0 g of the mixed salt oxybate. In some embodiments, the initial daily dose is about 4.5 g of the mixed salt oxybate.

In some embodiments, the titration comprises switching a patient from a once a day dose to a twice a day dose of the mixed salt oxybate. In some embodiments, the titration comprises switching a patient from a twice a day dose to a three times a day dose of the mixed salt oxybate. In some embodiments, the titration comprises switching a patient from a twice a day dose to a once a day dose of the mixed salt oxybate. In some embodiments, the titration comprises switching a patient from a three times a day dose to a twice a day dose of the mixed salt oxybate.

In some embodiments, the titration comprises administering ascending doses of the mixed salt oxybate. In some embodiments, the daily dose is increased every week until a dose that is effective and tolerated is achieved. In some embodiments, the daily dose is increased every other week until a dose that is effective and tolerated is achieved. In some embodiments, the daily dose is increased every third week until a dose that is effective and tolerated is achieved.

In some embodiments, the daily dose is increased on a weekly basis until a dose that is effective and tolerated is achieved. In some embodiments, the daily dose is increased once every week until a dose that is effective and tolerated is achieved. In some embodiments, the daily dose is increased twice every week until a dose that is effective and tolerated is achieved. In some embodiments, the daily dose is increased three times every week until a dose that is effective and tolerated is achieved. In some embodiments, the daily dose is increased four times every week until a dose that is effective and tolerated is achieved. In some embodiments, the daily dose is increased five times every week until a dose that is effective and tolerated is achieved. In some embodiments, the daily dose is increased six times every week until a dose that is effective and tolerated is achieved.

In some embodiments, the total weekly dose is increased by less than about 1.5 g of the mixed salt oxybate.

In some embodiments, the daily dose is increased every day until a dose that is effective and tolerated is achieved. In some embodiments, the daily dose is increased every other day until a dose that is effective and tolerated is achieved. In some embodiments, the daily dose is increased every second or third day until a dose that is effective and tolerated is achieved. In some embodiments, the daily dose is increased every third day until a dose that is effective and tolerated is achieved. In some embodiments, the daily dose is increased every second, third, or fourth day until a dose that is effective and tolerated is achieved. In some embodiments, the daily dose is increased every fourth day until a dose that is effective and tolerated is achieved. In some embodiments, the daily dose is increased every second, third, fourth, or fifth day until a dose that is effective and tolerated is achieved. In some embodiments, the daily dose is increased every fifth day until a dose that is effective and tolerated is achieved. In some embodiments, the daily dose is increased every second, third, fourth, fifth, or sixth day until a dose that is effective and tolerated is achieved. In some embodiments, the daily dose is increased every sixth day until a dose that is effective and tolerated is achieved. In some embodiments, the daily dose is increased every second, third, fourth, fifth, sixth, or seventh day until a dose that is effective and tolerated is achieved. In some embodiments, the daily dose is increased every seventh day until a dose that is effective and tolerated is achieved.

In some embodiments, the titration comprises increasing the daily dose by less than about 1.5 g of the mixed salt oxybate. In some embodiments, the titration comprises increasing the daily dose by about 0.25 g, about 0.5 g, about 0.75 g, about 1.0 g, about 1.25 g, about 1.5 g, about 1.75 g, or about 2.0 g of the mixed salt oxybate. In some embodiments, the titration comprises increasing the daily dose by about 1.0 g-1.5 g of the mixed salt oxybate.

In some embodiments, the daily dose is increased by about 0.5 g to 1.5 g per week. In some embodiments, the daily dose is increased by about 0.25 g to 1.5 g per week. In some embodiments, the daily dose is increased by less than about 1.5 g per week.

In some embodiments, the initial daily dose administered to a sodium oxybate naïve patient is about 3 grams, and is increased about 1.5 grams/night per week until a dose that is effective and tolerated is achieved. In some embodiments, the initial daily dose administered to a sodium oxybate naïve patient is less than or equal to about 3 grams, and is increased less than or equal to about 1.5 grams/night per week until a dose that is effective and tolerated is achieved. In some embodiments, the initial daily dose administered to a sodium oxybate naïve patient is about 3 grams, and is increased about 1.5 grams at weekly intervals until a dose that is effective and tolerated is achieved. In some embodiments, after a dose that is effective and tolerated is achieved in a sodium oxybate naïve patient the administered dose is further adjusted to optimize the patient's treatment. The dose may be optimized by the methods described herein (for example, up-titrating or down-titrating the dose, change the number of daily administrations, the patient's dose up or changing the division of the total nightly dosing). In some embodiments, the maximum daily dose administered to a sodium oxybate naïve patient is no more than about 6 grams. In some embodiments, the maximum daily dose administered to a sodium oxybate naïve patient is no more than about 6 grams is administered once nightly.

In some embodiments, the initial daily dose administered to a sodium oxybate naïve patient is about 4.5 grams, and is increased about 1.5 grams per night per week until a dose that is effective and tolerated is achieved. In some embodiments, the initial daily dose administered to a sodium oxybate naïve patient is less than or equal to about 4.5 grams, and is increased less than or equal to about 1.5 grams/night per week until a dose that is effective and tolerated is achieved. In some embodiments, the initial daily dose administered to a sodium oxybate naïve patient is about 4.5 grams, and is increased about 1.5 grams at weekly intervals until a dose that is effective and tolerated is achieved. In some embodiments, the initial daily dose administered to a sodium oxybate naïve patient is less than or equal to about 4.5 grams divided equally or unequally into 2 doses administered nightly. In some embodiments, after a dose that is effective and tolerated is achieved in a sodium oxybate naïve patient the administered dose is further adjusted to optimize the patient's treatment. The dose may be optimized by the methods described herein (for example, up-titrating or down-titrating the dose, change the number of daily administrations, the patient's dose up or changing the division of the total nightly dosing). In some embodiments, the maximum daily dose administered to a sodium oxybate naïve patient is no more than about 9 grams. In some embodiments, the maximum daily dose administered to a sodium oxybate naïve patient is no more than 9 grams divided equally or unequally into 2 doses administered nightly.

In some embodiments, the initial daily dose is 4.5 grams, and is increased 1.5 grams per night once per week until a dose that is effective and tolerated is achieved. In some embodiments, the initial daily dose is 4.5 grams, and is increased 1.5 grams at weekly intervals until a dose that is effective and tolerated is achieved. In some embodiments, after a dose that is effective and tolerated is achieved the administered dose is further adjusted to optimize the patient's treatment. The dose may be optimized by the methods described herein (for example, up-titrating or down-titrating the dose, change the number of daily administrations, the patient's dose up or changing the division of the total nightly dosing).

In some embodiments, the titration comprises administering descending doses of the mixed salt oxybate. In some embodiments, the daily dose is decreased every week until a dose that is effective and tolerated is achieved. In some embodiments, the daily dose is decreased every other week until a dose that is effective and tolerated is achieved. In some embodiments, the daily dose is decreased every third week until a dose that is effective and tolerated is achieved.

In some embodiments, the daily dose is decreased on a weekly basis until a dose that is effective and tolerated is achieved. In some embodiments, the daily dose is decreased once every week until a dose that is effective and tolerated is achieved. In some embodiments, the daily dose is decreased twice every week until a dose that is effective and tolerated is achieved. In some embodiments, the daily dose is decreased three times every week until a dose that is effective and tolerated is achieved. In some embodiments, the daily dose is decreased four times every week until a dose that is effective and tolerated is achieved. In some embodiments, the daily dose is decreased five times every week until a dose that is effective and tolerated is achieved. In some embodiments, the daily dose is decreased six times every week until a dose that is effective and tolerated is achieved.

In some embodiments, the daily dose is decreased every day until a dose that is effective and tolerated is achieved. In some embodiments, the daily dose is decreased every other day until a dose that is effective and tolerated is achieved. In some embodiments, the daily dose is decreased every second or third day until a dose that is effective and tolerated is achieved. In some embodiments, the daily dose is decreased every third day until a dose that is effective and tolerated is achieved. In some embodiments, the daily dose is decreased every second, third, or fourth day until a dose that is effective and tolerated is achieved. In some embodiments, the daily dose is decreased every fourth day until a dose that is effective and tolerated is achieved. In some embodiments, the daily dose is decreased every second, third, fourth, or fifth day until a dose that is effective and tolerated is achieved. In some embodiments, the daily dose is decreased every fifth day until a dose that is effective and tolerated is achieved. In some embodiments, the daily dose is decreased every second, third, fourth, fifth, or sixth day until a dose that is effective and tolerated is achieved. In some embodiments, the daily dose is decreased every sixth day until a dose that is effective and tolerated is achieved. In some embodiments, the daily dose is decreased every second, third, fourth, fifth, sixth, or seventh day until a dose that is effective and tolerated is achieved. In some embodiments, the daily dose is decreased every seventh day until a dose that is effective and tolerated is achieved.

In some embodiments, the titration comprises decreasing the daily dose by less than about 1.5 g of the mixed salt oxybate. In some embodiments, the titration comprises decreasing the daily dose by about 0.25 g, about 0.5 g, about 0.75 g, about 1.0 g, about 1.25 g, about 1.5 g, about 1.75 g, or about 2.0 g of the mixed salt oxybate. In some embodiments, the titration comprises decreasing the daily dose by about 1.0 g-1.5 g of the mixed salt oxybate.

In some embodiments, the daily dose is decreased by about 0.5 g to 1.5 g per week. In some embodiments, the daily dose is decreased by about 0.25 g to 1.5 g per week. In some embodiments, the daily dose is decreased by less than about 1.5 g per week. In some embodiments, the daily dose is decreased by about 0.5 g to 9.0 g per week. In some embodiments, the daily dose is decreased by about 0.25 g to 9.0 g per week.

In some embodiments, the initial daily dose is 4.5 grams, and is decreased 1.5 grams per night once per week until a dose that is effective and tolerated is achieved. In some embodiments, the initial daily dose is 4.5 grams, and is decreased 1.5 grams at weekly intervals until a dose that is effective and tolerated is achieved. In some embodiments, after a dose that is effective and tolerated is achieved the administered dose is further adjusted to optimize the patient's treatment. The dose may be optimized by the methods described herein (for example, up-titrating or down-titrating the dose, change the number of daily administrations, the patient's dose up or changing the division of the total nightly dosing).

In some embodiments, the titration is conducted from about 1 week to about 14 weeks.

In some embodiments, the mixed salt oxybate is administered three times per day. In some embodiments, the mixed salt oxybate is administered three times per day in equal doses. In some embodiments, the mixed salt oxybate is administered three times per day in unequal doses. In some embodiments, the mixed salt oxybate is administered twice per day. In some embodiments, the mixed salt oxybate is administered twice per day in equal doses. In some embodiments, the mixed salt oxybate is administered twice per day in unequal doses. In some embodiments, the mixed salt oxybate is administered once per day, See U.S. Ser. Nos. 16/688,797, 62/769,380 and 62/769,382. In some embodiments, the mixed salt oxybate is administered at bedtime. In some embodiments, the mixed salt oxybate is administered at bedtime and about 2.5 h-4 h after the bedtime administration. In some embodiments, the mixed salt oxybate is administered after a period of sleep. In some embodiments, the mixed salt oxybate is administered after a period of sleep and about 2.5 h-4 h later.

In some embodiments, the dose of the mixed salt oxybate is described in terms of the amount of the mixed salt oxybate that is administered to the patient. In some embodiments, about 0.25 g-10.0 g, about 1.0 g-9.0 g, about 2.0 g-10.0 g; about 3.0 g-9.5 g; or about 4.5 g-9.0 g of the mixed salt oxybate is administered per day.

In some embodiments, about 0.5 g-9 g of the mixed salt oxybate (such as JZP-258) is administered per day (e.g., as a single dose, or divided into 2 or 3 equal or unequal doses), including about 0.5 g, about 1.0 g, about 1.5 g, about 2.0 g, about 2.5 g, about 3.0 g, about 3.5 g, about 4.0 g, about 4.5 g, about 5.0 g, about 5.5 g, about 6.0 g, about 6.5 g, about 7.0 g, about 7.5 g, about 8.0 g, about 8.5 g, to about 9.0 g, including all values and ranges therebetween (e.g., about 6 g is administered once per day, or about 5 g to about 6 g is administered once per day). In some embodiments, about 2.0 g-9.0 g of the mixed salt oxybate (such as JZP-258) is administered once per day. In some embodiments, about 2.0 g-6.0 g of the mixed salt oxybate (such as JZP-258) is administered once per day. In some embodiments, about 4.5 g-6.0 g of the mixed salt oxybate (such as JZP-258) is administered once per day. In some embodiments, about 4.0 g-9.0 g of the mixed salt oxybate (such as JZP-258) is administered per day, wherein the mixed salt oxybate is administered in two equal or unequal doses. In some embodiments, about 0.5 g of the mixed salt oxybate (such as JZP-258) is administered per day. In some embodiments, about 0.5 g of the mixed salt oxybate (such as JZP-258) is administered once per day. In some embodiments, about 0.25 g of the mixed salt oxybate (such as JZP-258) is administered twice per day. In some embodiments, about 0.17 g of the mixed salt oxybate (such as JZP-258) is administered three times per day. In some embodiments, about 1.0 g of the mixed salt oxybate (such as JZP-258) is administered per day. In some embodiments, about 1.0 g of the mixed salt oxybate (such as JZP-258) is administered once per day. In some embodiments, about 0.5 g of the mixed salt oxybate (such as JZP-258) is administered twice per day. In some embodiments, about 0.33 g of the mixed salt oxybate (such as JZP-258) is administered three times per day. In some embodiments, about 1.5 g of the mixed salt oxybate (such as JZP-258) is administered per day. In some embodiments, about 1.5 g of the mixed salt oxybate (such as JZP-258) is administered once per day. In some embodiments, about 0.75 g of the mixed salt oxybate (such as JZP-258) is administered twice per day. In some embodiments, about 0.50 g of the mixed salt oxybate (such as JZP-258) is administered three times per day. In some embodiments, about 2.0 g of the mixed salt oxybate (such as JZP-258) is administered per day. In some embodiments, about 2.0 g of the mixed salt oxybate (such as JZP-258) is administered once per day. In some embodiments, about 1.0 g of the mixed salt oxybate (such as JZP-258) is administered twice per day. In some embodiments, about 0.66 g of the mixed salt oxybate (such as JZP-258) is administered three times per day. In some embodiments, about 2.5 g of the mixed salt oxybate (such as JZP-258) is administered per day. In some embodiments, about 2.5 g of the mixed salt oxybate (such as JZP-258) is administered once per day. In some embodiments, about 1.25 g of the mixed salt oxybate (such as JZP-258) is administered twice per day. In some embodiments, about 0.83 g of the mixed salt oxybate (such as JZP-258) is administered three times per day. In some embodiments, about 3.0 g of the mixed salt oxybate (such as JZP-258) is administered per day. In some embodiments, about 3.0 g of the mixed salt oxybate (such as JZP-258) is administered once per day. In some embodiments, about 1.5 g of the mixed salt oxybate (such as JZP-258) is administered twice per day. In some embodiments, about 1.0 g of the mixed salt oxybate (such as JZP-258) is administered three times per day. In some embodiments, about 3.5 g of the mixed salt oxybate (such as JZP-258) is administered per day. In some embodiments, about 3.5 g of the mixed salt oxybate (such as JZP-258) is administered once per day. In some embodiments, about 1.75 g of the mixed salt oxybate (such as JZP-258) is administered twice per day. In some embodiments, about 1.16 g of the mixed salt oxybate (such as JZP-258) is administered three times per day. In some embodiments, about 4.0 g of the mixed salt oxybate (such as JZP-258) is administered per day. In some embodiments, about 4.0 g of the mixed salt oxybate (such as JZP-258) is administered once per day. In some embodiments, about 2.0 g of the mixed salt oxybate (such as JZP-258) is administered twice per day. In some embodiments, about 1.32 g of the mixed salt oxybate (such as JZP-258) is administered three times per day. In some embodiments, about 4.5 g of the mixed salt oxybate (such as JZP-258) is administered per day. In some embodiments, about 4.5 g of the mixed salt oxybate (such as JZP-258) is administered once per day. In some embodiments, about 2.25 g of the mixed salt oxybate (such as JZP-258) is administered twice per day. In some embodiments, about 1.5 g of the mixed salt oxybate (such as JZP-258) is administered three times per day. In some embodiments, about 5.0 g of the mixed salt oxybate (such as JZP-258) is administered per day. In some embodiments, about 5.0 g of the mixed salt oxybate (such as JZP-258) is administered once per day. In some embodiments, about 2.5 g of the mixed salt oxybate (such as JZP-258) is administered twice per day. In some embodiments, about 1.7 g of the mixed salt oxybate (such as JZP-258) is administered is three times per day. In some embodiments, about 5.5 g of the mixed salt oxybate (such as JZP-258) is administered per day. In some embodiments, about 5.5 g of the mixed salt oxybate (such as JZP-258) is administered once per day. In some embodiments, about 2.75 g of the mixed salt oxybate (such as JZP-258) is administered twice per day. In some embodiments, about 1.8 g of the mixed salt oxybate (such as JZP-258) is administered three times per day. In some embodiments, about 6 g of the mixed salt oxybate (such as JZP-258) is administered per day. In some embodiments, about 6 g of the mixed salt oxybate (such as JZP-258) is administered once per day. In some embodiments, about 3.0 g of the mixed salt oxybate (such as JZP-258) is administered twice per day. In some embodiments, about 2.0 g of the mixed salt oxybate (such as JZP-258) is administered three times per day. In some embodiments, about 7.5 g of the mixed salt oxybate (such as JZP-258) is administered per day. In some embodiments, about 7.5 g of the mixed salt oxybate (such as JZP-258) is administered once per day. In some embodiments, about 3.75 g of the mixed salt oxybate (such as JZP-258) is administered twice per day. In some embodiments, about 2.5 g of the mixed salt oxybate (such as JZP-258) is administered three times per day. In some embodiments, about 9.0 g of the mixed salt oxybate (such as JZP-258) is administered per day. In some embodiments, about 9.0 g of the mixed salt oxybate (such as JZP-258) is administered once per day. In some embodiments, about 4.5 g of the mixed salt oxybate (such as JZP-258) is administered twice per day. In some embodiments, about 3.0 g of the mixed salt oxybate (such as JZP-258) is administered three times per day.

In some embodiments, the sodium oxybate is administered three times per day. In some embodiments, the sodium oxybate is administered three times per day in equal doses. In some embodiments, the sodium oxybate is administered three times per day in unequal doses. In some embodiments, the sodium oxybate is administered twice per day. In some embodiments, the sodium oxybate is administered twice per day in equal doses. In some embodiments, the sodium oxybate is administered twice per day in unequal doses. In some embodiments, the sodium oxybate is administered once per day, See U.S. Ser. Nos. 16/688,797, 62/769,380 and 62/769,382. In some embodiments, the sodium oxybate is administered at bedtime. In some embodiments, the sodium oxybate is administered at bedtime and about 2.5 h-4 h after the bedtime administration. In some embodiments, the sodium oxybate is administered after a period of sleep. In some embodiments, the sodium oxybate is administered after a period of sleep and about 2.5 h-4 h later.

In some embodiments, the dose of the sodium oxybate is described in terms of the amount of the sodium oxybate that is administered to the patient. In some embodiments, about 0.25 g-10.0 g, about 1.0 g-9.0 g, about 2.0 g-10.0 g; about 3.0 g-9.5 g; or about 4.5 g-9.0 g of the sodium oxybate is administered per day.

In some embodiments, about 0.5 g-9 g of the sodium oxybate is administered per day (e.g., as a single dose, or divided into 2 or 3 equal or unequal doses), including about 0.5 g, about 1.0 g, about 1.5 g, about 2.0 g, about 2.5 g, about 3.0 g, about 3.5 g, about 4.0 g, about 4.5 g, about 5.0 g, about 5.5 g, about 6.0 g, about 6.5 g, about 7.0 g, about 7.5 g, about 8.0 g, about 8.5 g, to about 9.0 g, including all values and ranges therebetween (e.g., about 6 g is administered once per day, or about 5 g to about 6 g is administered once per day). In some embodiments, about 2.0 g-9.0 g of the sodium oxybate is administered once per day. In some embodiments, about 2.0 g-6.0 g of the sodium oxybate is administered once per day. In some embodiments, about 4.5 g-6.0 g of the sodium oxybate is administered once per day. In some embodiments, about 4.0 g-9.0 g of the sodium oxybate is administered per day, wherein the sodium oxybate is administered in two equal or unequal doses. In some embodiments, about 0.5 g of the sodium oxybate is administered per day. In some embodiments, about 0.5 g of the sodium oxybate is administered once per day. In some embodiments, about 0.25 g of the sodium oxybate is administered twice per day. In some embodiments, about 0.17 g of the sodium oxybate is administered three times per day. In some embodiments, about 1.0 g of the sodium oxybate is administered per day. In some embodiments, about 1.0 g of the sodium oxybate is administered once per day. In some embodiments, about 0.5 g of the sodium oxybate is administered twice per day. In some embodiments, about 0.33 g of the sodium oxybate is administered three times per day. In some embodiments, about 1.5 g of the sodium oxybate is administered per day. In some embodiments, about 1.5 g of the sodium oxybate is administered once per day. In some embodiments, about 0.75 g of the sodium oxybate is administered twice per day. In some embodiments, about 0.50 g of the sodium oxybate is administered three times per day. In some embodiments, about 2.0 g of the sodium oxybate is administered per day.

In some embodiments, about 2.0 g of the sodium oxybate is administered once per day. In some embodiments, about 1.0 g of the sodium oxybate is administered twice per day. In some embodiments, about 0.66 g of the sodium oxybate is administered three times per day. In some embodiments, about 2.5 g of the sodium oxybate is administered per day. In some embodiments, about 2.5 g of the sodium oxybate is administered once per day. In some embodiments, about 1.25 g of the sodium oxybate is administered twice per day. In some embodiments, about 0.83 g of the sodium oxybate is administered three times per day. In some embodiments, about 3.0 g of the sodium oxybate is administered per day. In some embodiments, about 3.0 g of the sodium oxybate is administered once per day. In some embodiments, about 1.5 g of the sodium oxybate is administered twice per day. In some embodiments, about 1.0 g of the sodium oxybate is administered three times per day. In some embodiments, about 3.5 g of the sodium oxybate is administered per day. In some embodiments, about 3.5 g of the sodium oxybate is administered once per day. In some embodiments, about 1.75 g of the sodium oxybate is administered twice per day. In some embodiments, about 1.16 g of the sodium oxybate is administered three times per day. In some embodiments, about 4.0 g of the sodium oxybate is administered per day. In some embodiments, about 4.0 g of the sodium oxybate is administered once per day. In some embodiments, about 2.0 g of the sodium oxybate is administered twice per day. In some embodiments, about 1.32 g of the sodium oxybate is administered three times per day. In some embodiments, about 4.5 g of the sodium oxybate is administered per day. In some embodiments, about 4.5 g of the sodium oxybate is administered once per day. In some embodiments, about 2.25 g of the sodium oxybate is administered twice per day. In some embodiments, about 1.5 g of the sodium oxybate is administered three times per day. In some embodiments, about 5.0 g of the sodium oxybate is administered per day. In some embodiments, about 5.0 g of the sodium oxybate is administered once per day. In some embodiments, about 2.5 g of the sodium oxybate is administered twice per day. In some embodiments, about 1.7 g of the sodium oxybate is administered is three times per day. In some embodiments, about 5.5 g of the sodium oxybate is administered per day. In some embodiments, about 5.5 g of the sodium oxybate is administered once per day. In some embodiments, about 2.75 g of the sodium oxybate is administered twice per day. In some embodiments, about 1.8 g of the sodium oxybate is administered three times per day. In some embodiments, about 6 g of the sodium oxybate is administered per day. In some embodiments, about 6 g of the sodium oxybate is administered once per day. In some embodiments, about 3.0 g of the sodium oxybate is administered twice per day. In some embodiments, about 2.0 g of the sodium oxybate is administered three times per day. In some embodiments, about 7.5 g of the sodium oxybate is administered per day. In some embodiments, about 7.5 g of the sodium oxybate is administered once per day. In some embodiments, about 3.75 g of the sodium oxybate is administered twice per day. In some embodiments, about 2.5 g of the sodium oxybate is administered three times per day. In some embodiments, about 9.0 g of the sodium oxybate is administered per day. In some embodiments, about 9.0 g of the sodium oxybate is administered once per day. In some embodiments, about 4.5 g of the sodium oxybate is administered twice per day. In some embodiments, about 3.0 g of the sodium oxybate is administered three times per day.

In some embodiments, the dose of the mixed salt oxybate is described in terms of the amount of GHB that is administered to the patient. In some embodiments, a mixed salt oxybate (such as JZP-258) containing about 0.818 g-7.362 g, about 1.636 g-8.18 g; about 2.454 g-7.771 g; or about 3.681 g-7.362 g of GHB is administered per day.

In some embodiments, a mixed salt oxybate (such as JZP-258) containing about 0.818 g of GHB is administered per day. In some embodiments, a mixed salt oxybate (such as JZP-258) containing about 0.818 g of GHB is administered once per day. In some embodiments, a mixed salt oxybate (such as JZP-258) containing about 0.409 g of GHB is administered twice per day. In some embodiments, a mixed salt oxybate (such as JZP-258) containing about 0.273 g of GHB is administered three times per day.

In some embodiments, a mixed salt oxybate (such as JZP-258) containing about 2.454 g of GHB is administered per day. In some embodiments, a mixed salt oxybate (such as JZP-258) containing about 2.454 g of GHB is administered once per day. In some embodiments, a mixed salt oxybate (such as JZP-258) containing about 1.227 g of GHB is administered twice per day. In some embodiments, a mixed salt oxybate (such as JZP-258) containing about 0.818 g of GHB is administered three times per day.

In some embodiments, a mixed salt oxybate (such as JZP-258) containing about 3.681 g of GHB is administered per day. In some embodiments, a mixed salt oxybate (such as JZP-258) containing about 3.681 g of GHB is administered once per day. In some embodiments, a mixed salt oxybate (such as JZP-258) containing about 1.841 g of GHB is administered twice per day. In some embodiments, a mixed salt oxybate (such as JZP-258) containing about 1.227 g of GHB is administered three times per day.

In some embodiments, a mixed salt oxybate (such as JZP-258) containing about 4.908 g of GHB is administered per day. In some embodiments, a mixed salt oxybate (such as JZP-258) containing about 4.908 g of GHB is administered once per day. In some embodiments, a mixed salt oxybate (such as JZP-258) containing about 2.454 g of GHB is administered twice per day. In some embodiments, a mixed salt oxybate (such as JZP-258) containing about 1.636 g of GHB is administered three times per day.

In some embodiments, a mixed salt oxybate (such as JZP-258) containing about 6.135 g of GHB is administered per day. In some embodiments, a mixed salt oxybate (such as JZP-258) containing about 6.135 g of GHB is administered once per day. In some embodiments, a mixed salt oxybate (such as JZP-258) containing about 3.068 g of GHB is administered twice per day. In some embodiments, a mixed salt oxybate (such as JZP-258) containing about 2.045 g of GHB is administered three times per day.

In some embodiments, a mixed salt oxybate (such as JZP-258) containing about 7.362 g of GHB is administered per day. In some embodiments, a mixed salt oxybate (such as JZP-258) containing about 7.362 g of GHB is administered once per day. In some embodiments, a mixed salt oxybate (such as JZP-258) containing about 3.681 g of GHB is administered twice per day. In some embodiments, a mixed salt oxybate (such as JZP-258) containing about 2.454 g of GHB is administered three times per day.

In some embodiments, the mixed salt oxybate is administered with food. In some embodiments, the mixed salt oxybate composition is administered without food. In some embodiments, the mixed salt oxybate composition is administered with or without regard to food. In some embodiments, the mixed salt oxybate composition is administered without regard to food. In some embodiments, the patient is administered the mixed salt oxybate composition at least 2 h after the patient's last meal. In some embodiments, the patient is administered their first dose of the mixed salt oxybate composition at least 2 h after the patient's last meal. In some embodiments, the patient is administered their first dose of the mixed salt oxybate composition at least 2 h, at least 1.5 h, about 1.0 h, about 0.5 h or about 15 min after the patient's last meal. In some embodiments, the mixed salt oxybate is administered with or without regard to food after the titration period as described herein (i.e., when a stable dose of the mixed salt oxybate composition is achieved).

Although throughout the present disclosure, the amount of oxybate administered in a composition is generally expressed in terms of the amount of GHB administered (see above), the present disclosure contemplates embodiments where the oxybate dosing is expressed in the Equivalent Amount of GBA that is administered.

The Equivalent Amount of GBA in a compositions may be calculated by the following formula:

$$\text{Equivalent Amount of } GBA = \frac{\text{Amount of } GHB \text{ in (g)} \times 104.1 \left(\text{Formula Weight of } GBA, \frac{\text{g}}{\text{mol}}\right)}{103.1 \left(\text{Formula Weight of } GHB \left(\frac{\text{g}}{\text{mol}}\right)\right.}$$

In some embodiments, the dose of the mixed salt oxybate is described in terms of the amount of Equivalent Amount of GBA that is administered to the patient. In some embodiments, a mixed salt oxybate (such as JZP-258) containing about 0.826 g-7.434 g, about 1.652 g-8.26 g; about 2.478 g-7.847 g; or about 3.717 g-7.434 g of an Equivalent Amount of GBA is administered per day.

In some embodiments, a mixed salt oxybate (such as JZP-258) containing about 0.826 g of an Equivalent Amount of GBA is administered per day. In some embodiments, a mixed salt oxybate (such as JZP-258) containing about 0.413 g of an Equivalent Amount of GBA is administered twice per day. In some embodiments, a mixed salt oxybate (such as JZP-258) containing about 0.275 g of an Equivalent Amount of GBA is administered three times per day.

In some embodiments, a mixed salt oxybate (such as JZP-258) containing about 2.478 g of an Equivalent Amount of GBA is administered per day. In some embodiments, a mixed salt oxybate (such as JZP-258) containing about 1.239 g of an Equivalent Amount of GBA is administered twice per day. In some embodiments, a mixed salt oxybate (such as JZP-258) containing about 0.826 g of an Equivalent Amount of GBA is administered three times per day.

In some embodiments, a mixed salt oxybate (such as JZP-258) containing about 3.717 g of an Equivalent Amount of GBA is administered per day. In some embodiments, a mixed salt oxybate (such as JZP-258) containing about 1.859 g of an Equivalent Amount of GBA is administered twice per day. In some embodiments, a mixed salt oxybate (such as JZP-258) containing about 1.239 g of an Equivalent Amount of GBA is administered three times per day.

In some embodiments, a mixed salt oxybate (such as JZP-258) containing about 4.956 g of an Equivalent Amount of GBA is administered per day. In some embodiments, a mixed salt oxybate (such as JZP-258) containing about 2.478 g of an Equivalent Amount of GBA is administered twice per day. In some embodiments, a mixed salt oxybate (such as JZP-258) containing about 1.652 g of an Equivalent Amount of GBA is administered three times per day.

In some embodiments, a mixed salt oxybate (such as JZP-258) containing about 6.195 g of an Equivalent Amount of GBA is administered per day. In some embodiments, a mixed salt oxybate (such as JZP-258) containing about 3.098 g of an Equivalent Amount of GBA is administered twice per day. In some embodiments, a mixed salt oxybate (such as JZP-258) containing about 2.065 g of an Equivalent Amount of GBA is administered three times per day.

In some embodiments, a mixed salt oxybate (such as JZP-258) containing about 7.434 g of an Equivalent Amount of GBA is administered per day. In some embodiments, a mixed salt oxybate (such as JZP-258) containing about 3.717 g of an Equivalent Amount of GBA is administered twice per day. In some embodiments, a mixed salt oxybate (such as JZP-258) containing about 2.478 g of an Equivalent Amount of GBA is administered three times per day.

In some embodiments, the methods of the present disclosure comprise administering between 1 and 4.5 grams/day or between 6 and 10 grams/day of GHB. In some embodiments, the administered formulation comprises between 350-750 mg/ml or 450-550 mg/ml of GHB and has a pH between 6-10 or 6.5-8.

In some embodiments, the methods of the present disclosure comprise oral administration of the compositions or formulations comprising a mixed salt oxybate (disclosed herein) in a multiple dosage regimen. See U.S. Pat. No. 8,591,922, which is hereby incorporated by reference in its entirety for all purposes. In some embodiments, the multiple dosage regimen comprises one or more steps, as follows: (i) diluting an aqueous solution comprising about 500 mg/mL of the mixed salt oxybate with an aqueous medium to provide a first dose of about 1-10 grams of the mixture of salts; (ii) orally administering the dose to a patient; (iii) diluting an aqueous solution comprising about 500 mg/mL of the mixed salt oxybate to provide a second dose of about 1-10 grams of the mixed salt oxybate; and (iv) orally administering to the patient the second dose. The dose administered to the patient can be between about 0.25-9.0 grams. (All volumes and numbers are presented as Na GHB equivalents).

The embodiments are described in terms of administering a mixed salt oxybate composition; however, the present disclosure also contemplates the administration of the mixed salt oxybate in the compositions and formulations described herein. In some embodiments, the mixed salt composition is a liquid. In some embodiments, the concentration of the mixed salt in the liquid is from 50 mg/mL-950 mg/mL, about 250 mg/mL-750 mg/mL, about 350 mg/mL-650 mg/mL, or about 450 mg/mL-550 mg/mL. In some embodiments, the concentration of the mixed salt in the liquid is about 0.5 g/mL.

In one aspect, the present disclosure provides methods of treating a patient with IH comprising administering a sustained release oxybate composition to the patient with IH. In some embodiments, the sustained release composition comprises a mixed salt oxybate. In some embodiments, the composition comprises a sustained release composition described in U.S. Ser. No. 16/025,487 or U.S. Ser. No. 16/688,797, the contents of which is hereby incorporated by reference it entirety for all purposes.

The present disclosure provides, among other things, methods for administering a mixed salt oxybate to a patient with IH. Most patients with IH administered according to the methods described herein do not have cardiovascular disease or another condition (for example, high risk of stroke, renal impairment or hypertension) that would indicate them for treatment with a low sodium oxybate composition. However, in some embodiments, the patient administered the mixed salt oxybate is a patient at risk for the undesirable side effects related to high sodium intake. In some embodiments, the patient is in heart failure. In some embodiments, the patient is hypertensive. In some embodiments, the patient has renal impairment. In some embodiments, the patient is at risk for stroke.

In some embodiments, the patient is treated is treated for excessive daytime sleepiness in patients with idiopathic hypersomnia. See U.S. Pat. Nos. 6,472,431; 6,780,889; 7,262,219; 8,263,650; 8,461,203, 8,591,922, 8,901,173, 9,132,107, 9,555,017, 9,795,567, 10,195,168, U.S. Ser. Nos. 16/688,797, 62/769,380 and 62/769,382, and U.S. Patent Publication No. 2018/0263936 for example.

In some embodiments, a pharmacy management system may be required or preferred as part of a drug distribution program. For example, the present invention includes a method for distributing a drug containing GHB or a salt thereof to an approved pharmacy, the method comprising: (1) Identifying an approved pharmacy that has an established management system to dispense information concerning the risks associated with ingesting a MCT inhibitors concomitantly to said drug to patients that are prescribed said drug; (2) Providing said pharmacy with said information related to the risks; and (3) Authorizing distribution of said drug to said pharmacy, wherein said pharmacy dispenses the drug with said information when filling a prescription for said drug. The established management system may include an electronic alert to employees to dispense said information with said drug when prescriptions are filled. Such information may be dispensed in written form, for example in a brochure explaining the risks of concomitant ingestion of GHB and an MCT inhibitor such as diclofenac, valproate, or ibuprofen or combinations thereof. For example, the information dispensed with GHB may advise a patient of the potential for enhanced potency of GHB if the patient also takes valproate. Alternatively, or in addition thereto, the information dispensed with GHB may advise a patient of the potential for decreased potency of GHB if the patient also takes diclofenac. Such information may also be dispensed in verbal form. Distributors may maintain a directory of approved pharmacies, for example in a computer readable storage medium, to further ensure that GHB is dispensed only to patients who are advised of the additive effects.

A pharmacy management system of the present invention can be a REMS system as shown in U.S. Pat. Nos. 7,895,059; 7,797,171; 7,668,730 and 8,731,963. Warnings may be administered through the existing pharmacy management system as described in the patents above.

Methods of Making

The mixed salt oxybate, compositions and formulations may be prepared using methods that are known to those skilled in the art, including the methods described U.S. Pat. Nos. 8,591,922; 8,901,173; 9,132,107; 9,555,017; 10,195,168 and U.S. Publication No. 2018/0263936, which are hereby incorporated by reference.

EXAMPLES

Example 1

This is a double-blind, placebo-controlled, randomized withdrawal, multicenter study of the efficacy and safety of JZP-258 oral solution with an open-label safety extension period.

The study consists of the following periods:

- Screening Period for 14 to 30 days, with the option to rescreen once

- Open-label Treatment Titration and Optimization Period for 10 to 14 weeks
- Stable Dose Period for 2 weeks
- Double-blind Randomized Withdrawal Period for 2 weeks
- Open-label Safety Extension Period for 24 weeks
- Safety Follow-up Period for 2 weeks A subset of up to 30 subjects will participate in a single overnight PK evaluation during either the Open-label Treatment Titration and Optimization Period or the Open-label Safety Extension Period.

Efficacy Endpoints Will Include the Following:

- Epworth Sleepiness Scale ESS (primary endpoint), as assessed by the change in ESS score from the end of the Stable Dose Period to the end of the Double-blind Randomized Withdrawal Period.
- Patient Global Impression of change (PGIc; first key secondary endpoint), assessed by the proportion of subjects reporting worsening of symptoms (minimally worse, much worse, or very much worse) at the end of the Double-blind Randomized Withdrawal Period.
- Idiopathic Hypersomnia Severity Scale (IHSS; second key secondary endpoint): change in total score from the end of the Stable Dose Period to the end of the Double-blind Randomized Withdrawal Period.
- Clinical Global Impression of Change (CGIC): as assessed by the proportion of participants with worsening of symptoms at end of the Double-blind Randomized Withdrawal Period.
- Functional Outcomes of Sleep Questionnaire Short Version (FOSQ-10): as assessed by the change in total score from end of SDP to end of the Double-blind Randomized Withdrawal Period.

Exploratory Efficacy Endpoints Include the Following:

- Visual analog scale (VAS) for sleep inertia: as assessed by the change in mean daily score from last week of SDP to last week of the Double-blind Randomized Withdrawal Period.
- Total sleep time (TST): from daily sleep diary: change in the mean of the daily 24-hour TST from last week of SDP to last week of the Double-blind Randomized Withdrawal Period.
- Work Productivity and Activity Impairment Questionnaire: Specific Health Problem (WPAI:SHP): change in percent of work productivity and activity impairment from end of SDP to last week of DBRWP for the following endpoints:
  - Change in percent work time missed due to IH.
  - Change in percent impairment while working due to IH.
  - Change in percent overall work impairment due to IH
  - Change in percent activity impairment due to IH.

Safety assessments will include AE monitoring, vital signs, physical examinations, 12-lead ECG, clinical laboratory tests, and the Columbia Suicide Severity Rating Scale (C-SSRS).

Screening Period (14 to 30 Days)

All subjects will be evaluated for eligibility during the Screening Period, which will occur over a period of 14 to 30 days.

Open-label Treatment Titration and Optimization Period (10 to 14 weeks) ("OTTP")

The aim of JZP-258 dose titration and optimization is to maximize efficacy (improved IH symptoms, e.g., EDS, sleep inertia and sleep duration) while ensuring adequate nocturnal sleep and minimizing risk associated with safety and tolerability.

Day 1 of the study will occur the day drug is dispensed at the Baseline Visit. During the Open-label Treatment Titration and Optimization Period subjects will either transition from Xyrem to JZP-258, or initiate treatment with JZP-258, based on treatment status at study entry:

Subjects who are on a stable dose of Xyrem at study entry will switch from Xyrem to the same dosing regimen of JZP-258. The dosing regimen of JZP-258 may be adjusted until an optimally effective and tolerable dosing regimen is established.

Subjects who are not on Xyrem at study entry will initiate JZP-258 either as a once or twice nightly dosing regimen at the discretion of the investigator. The dosing regimen of JZP-258 may be adjusted until an optimally effective and tolerable dose regimen is established.

The Medical Monitor should be contacted with any questions related to dosing and titration.

All subjects will undergo at minimum a 10-week Open-label Treatment Titration and Optimization Period even if the optimized dosing regimen is achieved earlier. Every effort should be made to titrate to an optimally effective and tolerable dosing regimen within the first 8 weeks, and maintain an unchanged dose of JZP-258 for at least 2 weeks prior to entering the Stable Dose Period. Any subject for whom an efficacious and tolerable dosing regimen is not established within the first 10 weeks may undergo up to an additional 4 weeks of titration/adjustment with approval from the Medical Monitor. Subjects who are unable to attain an efficacious and tolerable dosing regimen after 14 weeks will be withdrawn from the study.

Subjects who have reached an optimized dosing regimen, and who have completed the Open label Treatment Titration and Optimization Period, will then enter the 2-week Stable Dose Period and remain on that dosing regimen throughout the Stable Dose Period.

Stable Dose Period (2 Weeks) (“SDP”)

Subjects will remain on the stable JZP-258 dose, unchanged, during this 2-week period. Upon completion of the Stable Dose Period, subjects will be assessed for randomization eligibility.

Double-Blind Randomized Withdrawal Period (2 Weeks) (“DBRW”)

Subjects who meet the randomization criteria at the end of the Stable Dose Period will be randomized 1:1 to receive 1 of the following 2 treatments during the 2-week Double-blind Randomized Withdrawal Period.

JZP-258: Active JZP-258 will be continued as a double-blind treatment at the stable dose and regimen for 2 weeks Placebo: Placebo will be initiated as a double-blind treatment at a volume and regimen equivalent to the JZP-258 dose and regimen for 2 weeks Randomization will be stratified by the subject’s use of stimulant agent and/or Xyrem at baseline per the following baseline medication groups: 1) subjects on Xyrem only; 2) subjects on Xyrem and an additional stimulant or alerting agent; 3) subjects not currently taking Xyrem but are taking a stimulant or alerting agent; or 4) subjects not currently taking Xyrem or a stimulant or alerting agent.

Based on enrollment, an optional interim analysis (IA) may be conducted when approximately 60% of the 112 planned randomized subjects have completed or are early terminated from the Double-blind Randomized Withdrawal Period. If the predefined efficacy stopping rule is met, per Data Monitoring Committee (DMC) communication, enrollment and randomization to placebo treatment may stop. All subjects who have not already been randomized would then receive open-label JZP-258 during the Double-blind Randomized Withdrawal Period. All subjects who have already entered the Double-blind Randomized Withdrawal Period will complete that period as planned.

Open-Label Safety Extension Period (24 Weeks) (“OLE”)

Subjects who complete the Double-blind Randomized Withdrawal Period will enter a 24-week Open-label Safety Extension Period. Subjects will start the Open-label Safety Extension Period at a dose no higher than the dose they received at the end of the Stable Dose Period. A lower starting dose will be allowed at the discretion of the Investigator. If further titration is required, it will proceed at a rate of ≤1.5 g per night per week during this period, not to exceed a maximum total dose of 9 g/night. In the event that randomization to placebo is stopped after the IA, subjects will continue to take an effective and tolerable dose during the Open-label Safety Extension Period.

Safety Follow-Up Period (2 Weeks)

A Safety Follow-up visit will occur 2 weeks after the Open-label Safety Extension Period (completion of study).

Pharmacokinetic Study (1 Night in Open-Label Treatment Titration and Optimization Period or Open-Label Safety Extension Period)

A subset of up to 30 subjects will have the option to participate in a single overnight PK evaluation during either the Open-label Treatment Titration and Optimization Period or the Open-label Safety Extension Period. The PK evaluation night may occur on any night during 1 of the 2 periods, but preferably during 1 of the scheduled in-clinic visits. Subjects who are dosing JZP-258 on a once or twice nightly dosing regimen may be eligible to participate.

Subjects who choose to participate will take their currently assigned dose(s) at similar conditions to those normally followed at home. Subjects will take the first nightly dose at their normal bedtime. If a subject eats during the PK study, the timings for meal, snack, and doses must be recorded in the source document and the electronic case report form (eCRF).

Treatment Initiation and Titration

During the Open-label Treatment Titration and Optimization Period subjects will either transition from Xyrem to JZP-258, or initiate treatment with JZP-258, based on treatment status at study entry:

1. Subjects who are on a stable dose of Xyrem at study entry will switch from Xyrem to the same dosing regimen of JZP-258. The dosing regimen of JZP-258 then may be adjusted until an optimally effective and tolerable dosing regimen is established.

Subjects who are not on Xyrem at study entry will initiate JZP-258 either as a once nightly or twice nightly dosing regimen at the discretion of the investigator. The dosing regimen of JZP-258 may be adjusted until an optimally effective and tolerable dosing regimen is established.

The aim of JZP-258 dose titration and optimization is to maximize efficacy (reduction in IH symptoms, e.g., EDS, sleep inertia, and long sleep duration) while ensuring adequate nocturnal sleep and minimizing risk associated with safety and tolerability. The Medical Monitor should be contacted with any questions related to dosing and titration.

Subjects Starting Once Nightly Dosing Regimen

Subjects who report difficulty awakening as a result of significant sleep inertia or long sleep time (>11 hours/24 hours) may be considered for a once nightly dosing regimen at the discretion of the investigator. For subjects who initiate dosing JZP-258 as a once nightly dosing regimen, the starting dose should not exceed 3 g, the maximal single dose should not exceed 6 g, and the maximum nightly dose should not exceed 9 g. Titration should proceed at a rate of ≤1.5 g/night per week with incremental increases every few days as tolerated. The dose should be taken at bedtime. If a subject develops treatment associated sleep inadequacy on a single nightly dose, the dose may be taken after an initial period of sleep.

Subjects who initiate JZP-258 as a once nightly dosing regimen may switch to a twice nightly dosing regimen to optimize efficacy and tolerability, or to ensure adequate sleep duration. When switching to the twice nightly dosing regimen, the total nightly dose should be the same or no more than 1.5 g higher than the current dose. The first dose will be administered at bedtime or after an initial period of sleep and the second dose should be administered 2.5 to 4 hours later. Titration should proceed at a rate of ≤1.5 g/night per week, as required for optimal efficacy and tolerability; the increase in dose can be made incrementally as tolerated. The total nightly dose should not exceed 9 g/night. The maximal single dose should not exceed 6 g/night. The dose may be reduced at any time, as needed, for tolerability.

Subjects Starting Twice Nightly Dosing Regimen

Subjects who report disrupted nighttime sleep or difficulty maintaining sleep may be considered for a twice nightly dosing regimen at the discretion of the investigator.

For subjects who initiate JZP-258 as a twice nightly dosing regimen, the starting dose should not exceed 4.5 g/night divided into 2 doses (2.25 g each). The first dose will be administered at bedtime or after an initial period of sleep; the second dose should be administered 2.5 to 4 hours later. Titration should proceed at a rate of ≤1.5 g/night per week, as required for optimal efficacy and tolerability; the increase in dose can be made incrementally as tolerated. The maximal single dose should not exceed 6 g, and the total nightly dose should not exceed 9 g. The dose may be reduced at any time, as needed, for tolerability. If the subject does not achieve adequate sleep duration, the first dose may be taken after an initial period of sleep.

Subjects who initiate JZP-258 as a twice nightly dosing regimen may switch to once nightly if they are unable to wake up to take the second dose, or have difficulty awakening from sleep in the morning. The same first dose taken in the twice nightly dose regimen may be the starting dose when switching to once nightly dosing regimen. Titration should then proceed at a rate of ≤1.5 g/night per week. The maximal once nightly dose may not exceed 6 g.

While most subjects should be able to achieve an efficacious and tolerable dose while maintaining adequate sleep duration with a twice-nightly dosing regimen, in some instances there may be subjects who still are not maintaining adequate sleep duration. In these instances, subjects may divide their nightly dose into 3 administrations to ensure adequate sleep duration. In these cases, the same dosing intervals (2.5 to 4 hours), titration schedule (<1.5 g/night per week) and total nightly dose (9 g) remain applicable (See Table 1).

TABLE 1

JZP-258 Dosing Recommendations

| Dosing Regimen | Starting Nightly Dose[d] | Titration Increments[a] | Nightly Dose[b] |
|---|---|---|---|
| Once Nightly | ≤3 g | ≤1.5 g/night per week | 6 g |
| Twice Nightly | ≤4.5 g (divided) | ≤1.5 g/night per week | 9 g |
| Thrice Nightly[c] (titration only, not a starting dose) | Not applicable | ≤1.5 g/night per week | 9 g |

NOTE:

the aim of JZP-258 dose titration and optimization is to maximize efficacy (reduced IH symptoms, e.g., EDS, sleep inertia, and sleep duration) while ensuring adequate nocturnal sleep and minimizing risks associated with safety and tolerability.

[a]The weekly increase in dose of ≤1.5 g night may be made incrementally every few days as tolerated.

[b]The maximum single dose should not exceed 6 g and the maximum nightly dose should not exceed 9 g at twice or thrice nightly dosing

[c]Participants could adjust dosing to thrice nightly after initiating at twice nightly (no timing was specified in the protocol) if needed to optimize efficacy, tolerability, or sleep duration.

EDS = excessive daytime sleepiness;

IH = idiopathic hypersomnia.

[d]For participants who are not taking sodium oxybate at study entry

Subjects will be instructed to take each dose while in bed and remain in bed after each dose. Subjects will also be instructed to complete a daily dosing diary. For all dosing regimens, investigators should caution subjects about operating hazardous machinery, including automobiles or airplanes until subjects are reasonably certain that the study drug does not affect them adversely (e.g., impair judgment, thinking or motor skill). The study allowed for dosing without regard to food.

Results

A total of 154 patients were enrolled in the study, and 115 patients were randomized (56 patients in the JZP-258 treatment group, 59 patients in the placebo treatment group). The demographics and baseline characteristics of patients in the study are depicted in Table 2. The baseline disease characteristics of the patients in the study are depicted in Table 3. Characteristics were well balanced between randomized treatment groups and consistent with the Safety Analysis Set.

TABLE 2

Demographics and Baseline Characteristics

| | Safety Analysis Set N = 154 |
|---|---|
| Age (years) | |
| Mean (SD) | 40.3 (13.73) |
| Median (min, max) | 39.0 (19, 75) |
| Gender, n (%) | |
| Male | 49 (31.8) |
| Female | 105 (68.2) |
| Region, n (%) | |
| North America | 104 (67.5) |
| Europe | 50 (32.5) |
| Baseline Medication Group at study entry, n (%) | |
| Xyrem | 2 (1.3) |
| Xyrem + Stimulant or Alerting Agent | 4 (2.6) |
| Stimulant or Alerting Agent Only | 82 (53.2) |
| Naïve | 66 (42.9) |

TABLE 3

Baseline Disease Characteristics

| | Safety Analysis Set N = 154 |
|---|---|
| Baseline ESS | |
| Mean (SD) | 16.1 (3.59) |
| Median (min, max) | 16.5 (0, 23) |
| Baseline IHSS | |
| Mean (SD) | 32.1 (7.97) |
| Median (min, max) | 33 (5, 48) |
| Baseline CGIs | |
| Normal, not at all ill | 0 |
| Borderline ill | 1 (0.6) |
| Mildly ill | 4 (2.6) |
| Moderately ill | 55 (35.7) |
| Markedly ill | 63 (40.9) |
| Severely ill | 30 (19.5) |
| Among the most Extremely ill | 1 (0.6) |

The safety profile of JZP-258 was consistent with that of oxybate.

The primary endpoint of Epworth Sleepiness Scale (ESS) score was assessed by the change in the ESS score from the end of the Stable Dose Period to the end of the Double-blind Randomized Withdrawal Period in JZP-258 and placebo treatment groups and is presented in Table 4. The Mean ESS across the study by randomized treatment in the mITT population is depicted in FIG. 1.

With JZP-258 treatment, patients showed substantial improvements in ESS score during the open-label titration period prior to randomization (FIG. 1).

During the randomized withdrawal portion of the trial, patients administered JZP-258 showed clinically meaningful maintenance of efficacy for the primary endpoint ESS score. There was a significant worsening in patients randomized to placebo compared with patients randomized to JZP-258 for ESS (p-value <0.0001).

During the Open-Label Safety Extension Period, maintenance of efficacy was observed in patients who had been randomized to JZP-258 and continued JZP-258 treatment during the Open-Label Safety Extension Period (FIG. 1). In addition, as shown in FIG. 1, when placebo-treated patients from the randomized withdrawal portion of the study were switched to JZP-258-treatment for the Open-Label Safety Extension Period, a significant and sustained improvement in mean ESS was observed.

TABLE 4

Change in ESS (mITT population)

| Analysis of Primary Efficacy Endpoint | JZP-258 N = 56 | Placebo N = 59 |
|---|---|---|
| End of Stable-Dose Period (Baseline) | | |
| Mean (SD) | 6.3 (4.33) | 5.8 (3.66) |
| Median (Q1, Q3) | 6.5 (2.0, 9.5) | 5.0 (3.0, 8.0) |
| Min, Max | 0, 15 | 0, 17 |
| End of Double blind Randomized withdrawal Period | | |
| Mean (SD) | 7.0 (5.03) | 13.3 (4.06) |
| Median (Q1, Q3) | 7.0 (3.0, 10.0) | 14.0 (11.0, 16.0) |
| Min, Max | 0, 21 | 3, 21 |

TABLE 4-continued

Change in ESS (mITT population)

| Analysis of Primary Efficacy Endpoint | JZP-258 N = 56 | Placebo N = 59 |
|---|---|---|
| Change from SDP to DBRWP | | |
| Mean (SD) | 0.7 (3.22) | 7.4 (5.16) |
| Median (Q1, Q3) | 0.0 (−0.5, 1.0) | 8.0 (3.0, 11.0) |
| Min, Max | −6, 10 | −4, 18 |
| LS Mean Difference (95% CI)* | −6.51 (−7.99, −5.03) | |
| p-value | <0.0001 | |

*Based on an ANCOVA model including End SDP ESS, baseline medication group, and treatment as covariates; the corresponding p-value for the treatment covariate is reported. LS mean difference estimates JZP-258 − Placebo The PGIc secondary efficacy endpoint was assessed by the proportion of subjects reporting worsening of symptoms (minimally worse, much worse, or very much worse) at the end of the Double-blind Randomized Withdrawal Period.

Figure 2:
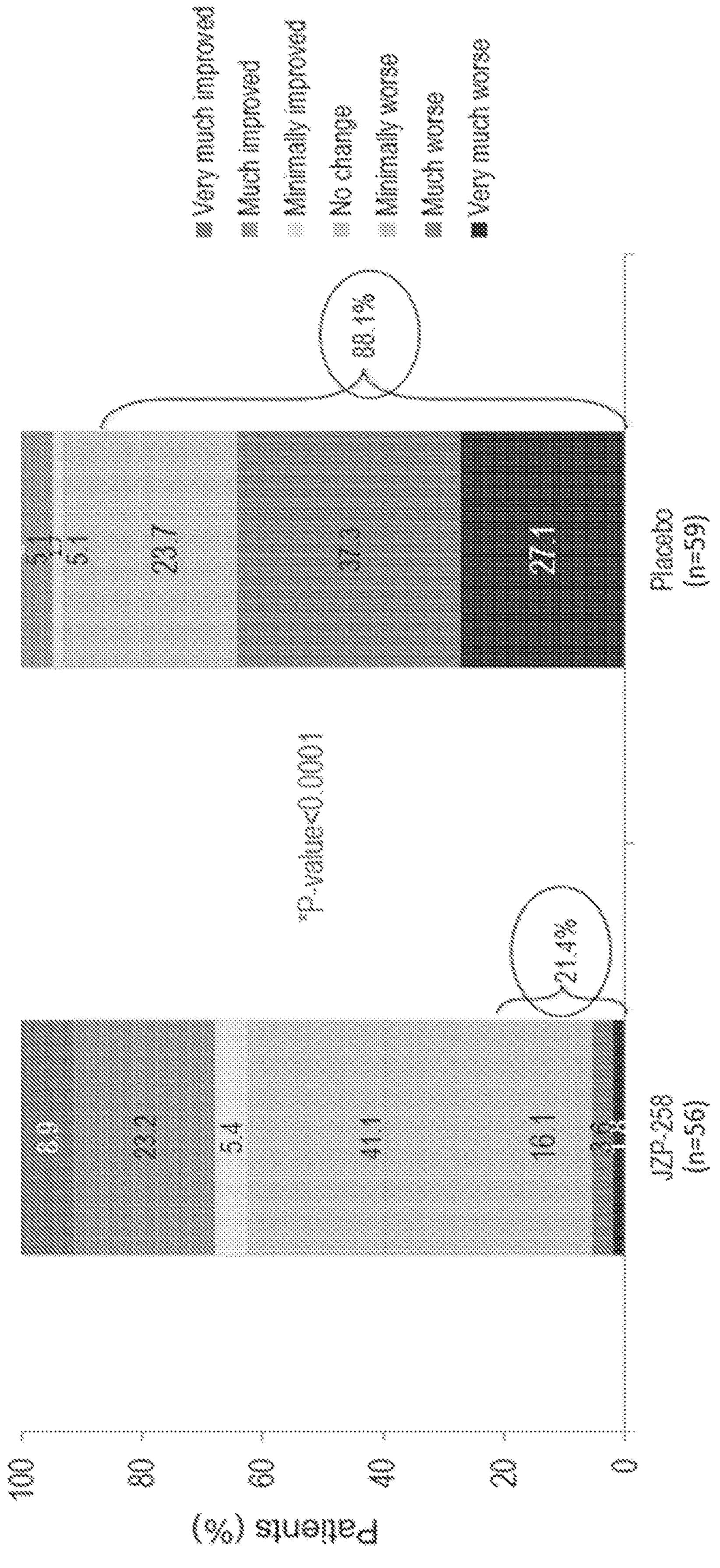
FIG. 2 shows the Patient Global Impression of change (PGIc) for patients treated with JZP-258 and patients treated with placebo at the end of the Double-blind Randomized Withdrawal Period in the study described in Example 1 (p-value<0.0001). *The p-value for comparing the proportion worsened on the PGIc between treatments is from a Cochran-Mantel-Haenszel (CMH) test stratified by baseline medication group.

During the randomized withdrawal portion of the trial, patients administered JZP-258 showed clinically meaningful maintenance of efficacy in the key PGIc secondary endpoint. As shown in FIG. 2 there was a significant worsening of symptoms in patients randomized to placebo compared with patients randomized to JZP-258. At the end of the Double-blind Randomized Withdrawal Period 88.1% of the patients randomized to placebo reported worsening symptoms, whereas only 21.4% of the patients randomized to JZP-258 reported worsening symptoms (p value <0.0001).

The key IHSS secondary efficacy endpoint was assessed by the change in total score from the end of the Stable Dose Period to the end of the Double-blind Randomized Withdrawal Period in JZP-258 and placebo treatment groups in the modified intent-to-treat (mITT) population and is presented in Table 5. The Mean IHSS across the study by randomized treatment in the mITT population is depicted in FIG. 3.

Figure 3:
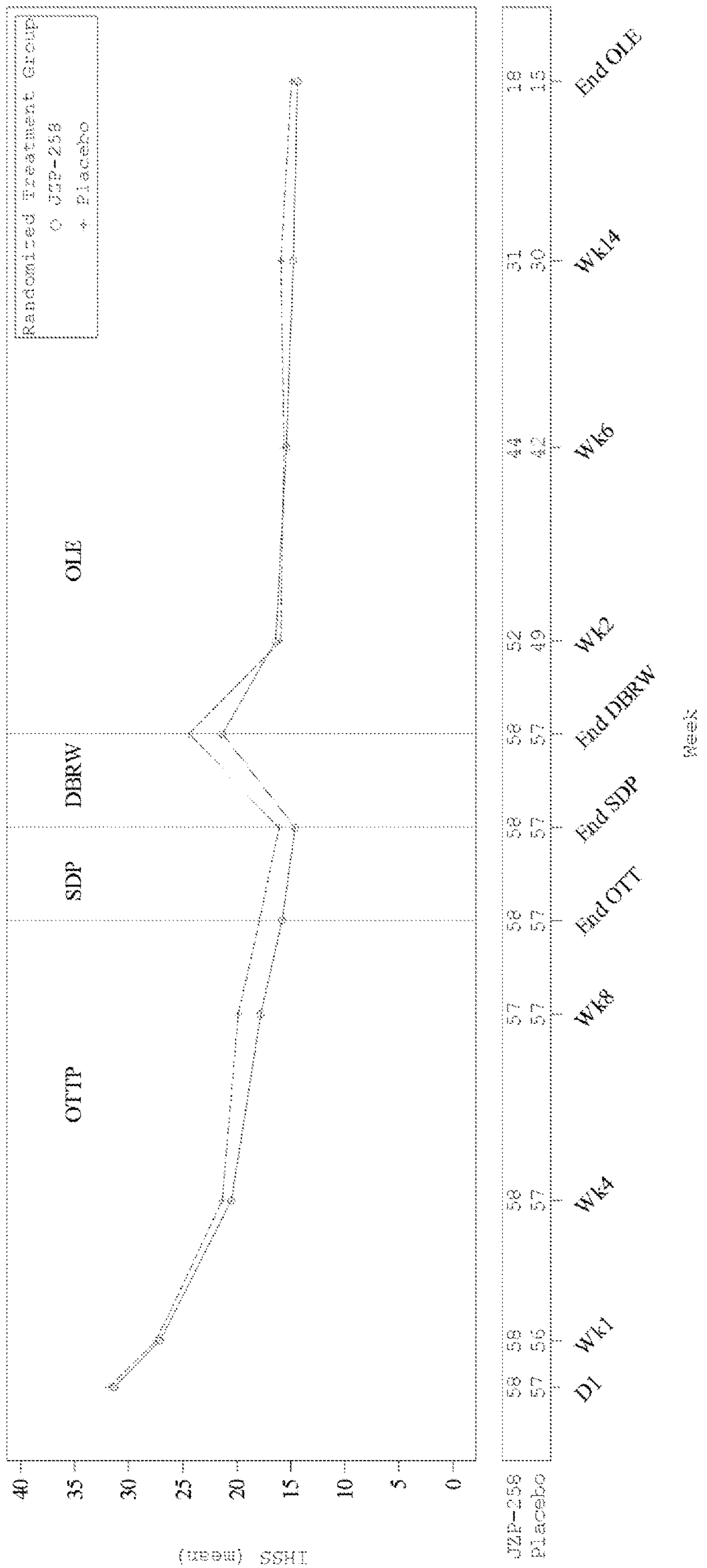
FIG. 3 shows the mean Idiopathic Hypersomnia Severity Scale (IHSS) score during the study described in Example 1 for patients treated with JZP-258 and patients treated with placebo.

With JZP-258 treatment, patients showed substantial improvements in mean IHSS during the open-label titration period prior to randomization (FIG. 3).

During the randomized withdrawal portion of the trial, patients administered JZP-258 showed clinically meaningful maintenance of efficacy for the key secondary endpoint of Idiopathic Hypersomnia Severity Scale (IHSS). There was a significant worsening in patients randomized to placebo compared with patients randomized to JZP-258 for IHSS (p-value <0.0001).

TABLE 5

Change in IHSS (mITT population)

| Analysis of Key Secondary Efficacy Endpoint | JZP-258 N = 56 | Placebo N = 59 |
|---|---|---|
| End of Stable-Dose Period (Baseline) | | |
| Mean (SD) | 15.5 (9.20) | 15.2 (7.78) |
| Median (Q1, Q3) | 14.0 (7.0, 22.0) | 14.0 (10.0, 21.0) |
| Min, Max | 1, 39 | 2, 37 |
| End of Double blind Randomized withdrawal Period | | |
| Mean (SD) | 16.9 (8.09) | 28.5 (8.96) |
| Median (Q1, Q3) | 16.0 (11.0, 23.0) | 29.0 (23.0, 34.0) |
| Min, Max | 1, 34 | 8, 49 |

TABLE 5-continued

| Change in IHSS (mITT population) | | |
|---|---|---|
| Analysis of Key Secondary Efficacy Endpoint | JZP-258 N = 56 | Placebo N = 59 |
| Change from SDP to DBRWP | | |
| Mean (SD) | 1.5 (5.82) | 13.3 (9.29) |
| Median (Q1, Q3) | 0 (−2.0, 2.5) | 14.0 (4.0, 19.0) |
| Min, Max | −8, 24 | −2, 38 |
| Estimated Median Difference (95% CI)* | −12.00 (−15.0, −8.0) | |
| p-value** | <0.0001 | |

*Hodges-Lehman estimate for JZP-258 − Placebo

**Rank based ANCOVA model including End SDP IHSS, baseline medication group, and treatment as covariates; the corresponding p-value for the treatment covariate is reported.

Figure 4:
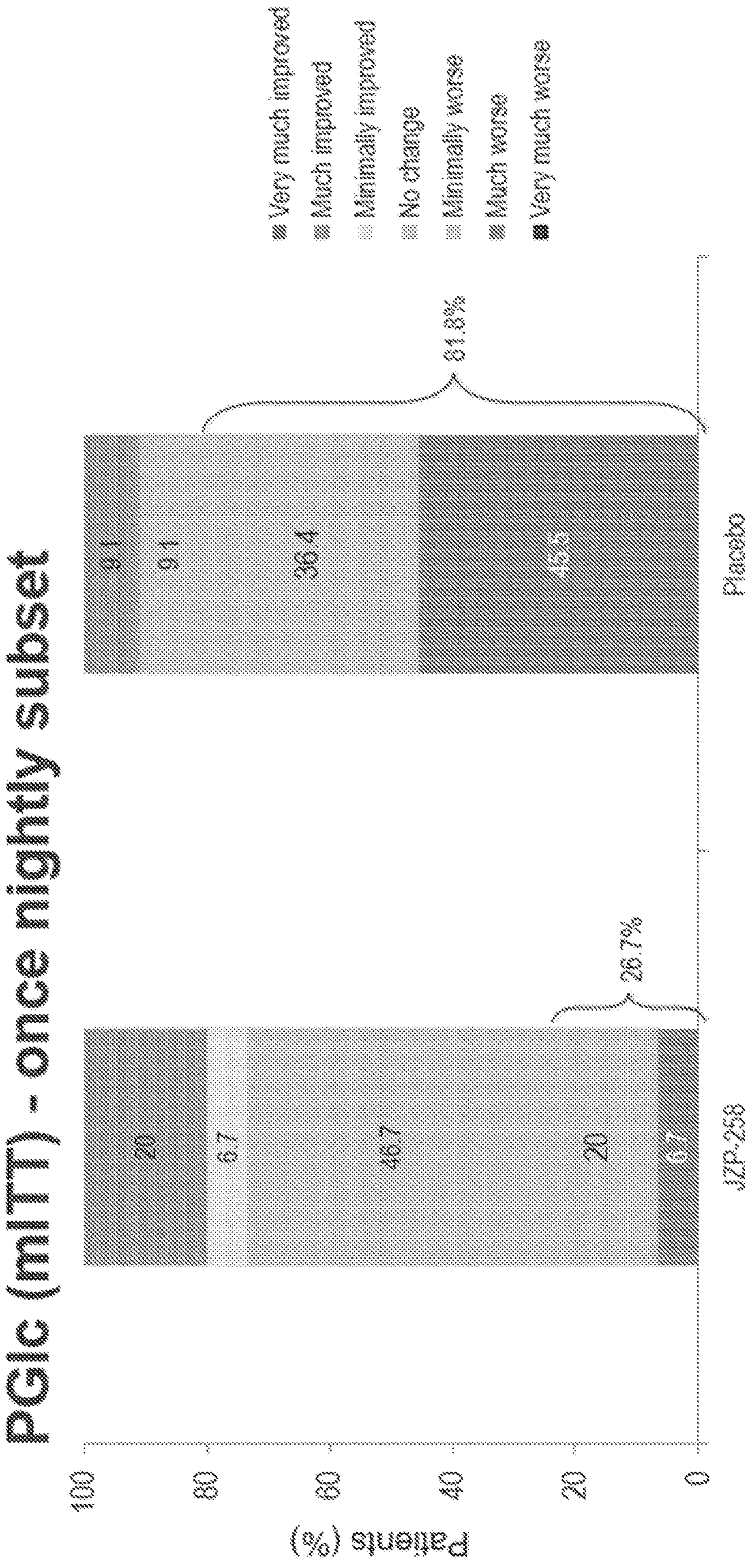
FIG. 4 shows the PGIc in the once nightly subset (patients treated once nightly with JZP-258 (n=15) and patients treated once nightly with placebo (n=11)) at the end of the Double-blind Randomized Withdrawal Period in the modified intent-to-treat (mITT) population from the study described in Example 1.
Figure 5:
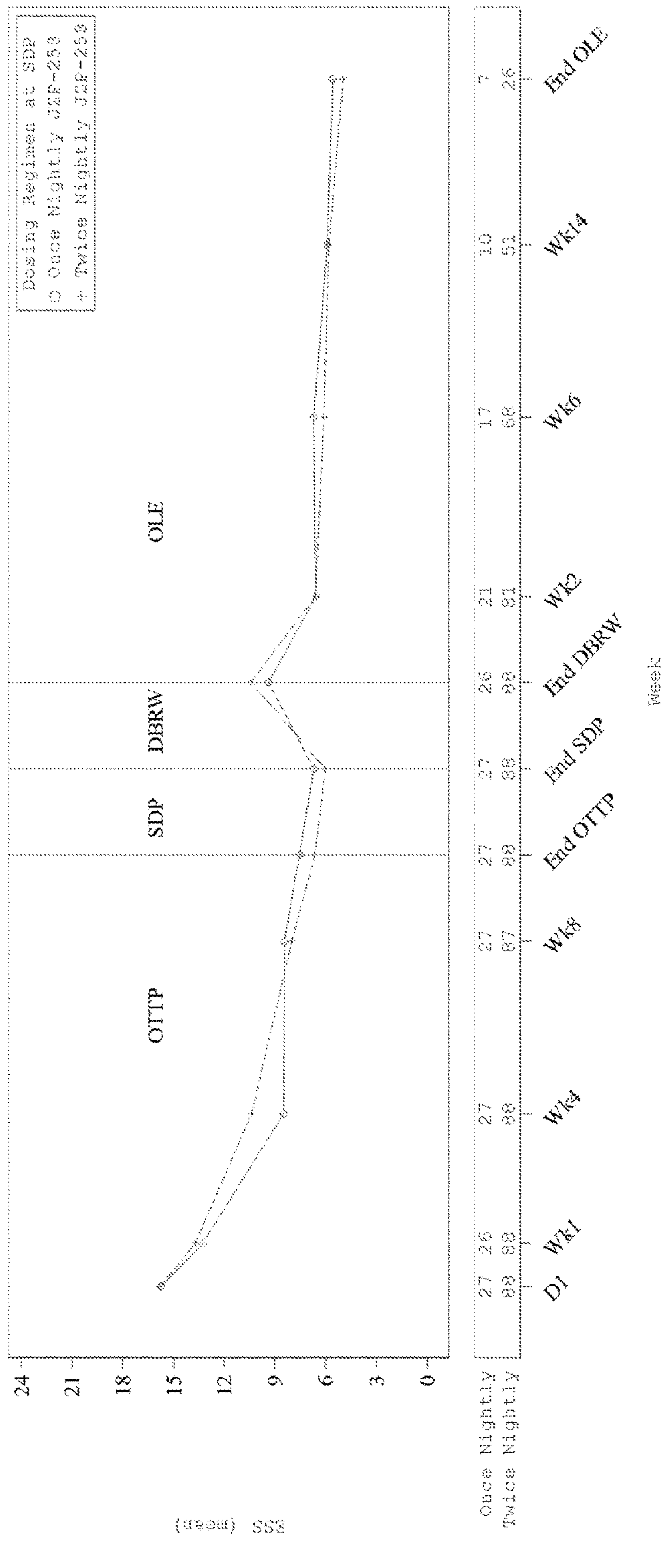
FIG. 5 shows the change in mean ESS score during the study described in Example 1 for patients treated once nightly with JZP-258 and patients treated twice nightly with JZP-258 (mITT population) during the Stable Dose Phase.

In this study JZP-258 treatment was initiated as either a once or twice nightly dosing regimen, followed by titration to an optimally effective and tolerable dose within the regimen, to the other regimen, or to thrice nightly administration. At the time of the Stable Dose Period ~75% of participants were on a twice nightly dosing regimen of JZP-258, and 25% were on a once nightly dosing regimen. The change in ESS score by Stable Dose Regimen in the mITT population in shown in Table 6. The PGIc in the once nightly subset of the patients in the mITT population is shown in FIG. 4. The study showed that change in ESS over the DBRWP was similar to that of patients taking the twice nightly regimen. The disease burden at baseline was similar for patients talking once nightly and twice nightly regimens. The change in ESS over the OLOTTP and SDP was similar for patients taking once nightly and twice nightly regimens (FIG. 5). In addition, 33 patients in the study were exposed to single doses of >4.5 g. The Median (min, max) exposure duration to doses >4.5 g was 73 days (1, 276).

TABLE 6

| Subgroup Analysis of Change in ESS by Stable Dose Regimen (mITT) | | | | |
|---|---|---|---|---|
| | Once nightly N = 26 | | Twice nightly N = 88 | |
| | JZP-258 | Placebo | JZP-258 | Placebo |
| n | 15 | 11 | 41 | 47 |
| Mean (SD) | 0.9 (2.22) | 5.6 (3.07) | 0.6 (3.54) | 7.7 (5.45) |
| Median | 1.0 | 5.0 | 0.0 | 8.0 |
| Q1, Q3 | 0.0, 3.0 | 3.0, 9.0 | −1.0, 1.0 | 4.0, 11.0 |
| Min., Max. | −4, 4 | 1, 10 | −6, 10 | −4, 18 |

Conclusions

The results from this study demonstrate the efficacy of JZP-258 for the treatment of IH. All clinical endpoints were met. Patients entering the study had excessive daytime sleepiness typical of the idiopathic hypersomnia population. With JZP-258 treatment, patients showed substantial improvements during the open-label titration period prior to randomization. During the randomized withdrawal portion of the trial, patients randomized to JZP-258 showed clinically meaningful maintenance of efficacy for the primary endpoint of Epworth Sleepiness Scale (ESS) score and the key secondary endpoints of the change in Patient Global Impression of Change (PGIc) scores and Idiopathic Hypersomnia Severity Scale (IHSS). There was a significant worsening in patients administered placebo compared with JZP-258 for ESS (p-value <0.0001), PGIc (p-value <0.0001) and IHSS (p-value <0.0001). No new safety signals for JZP-258 were observed in patients with IH and the overall safety profile of JZP-258 was consistent with that reported for sodium oxybate (Xyrem).

Example 2

Figure 6:
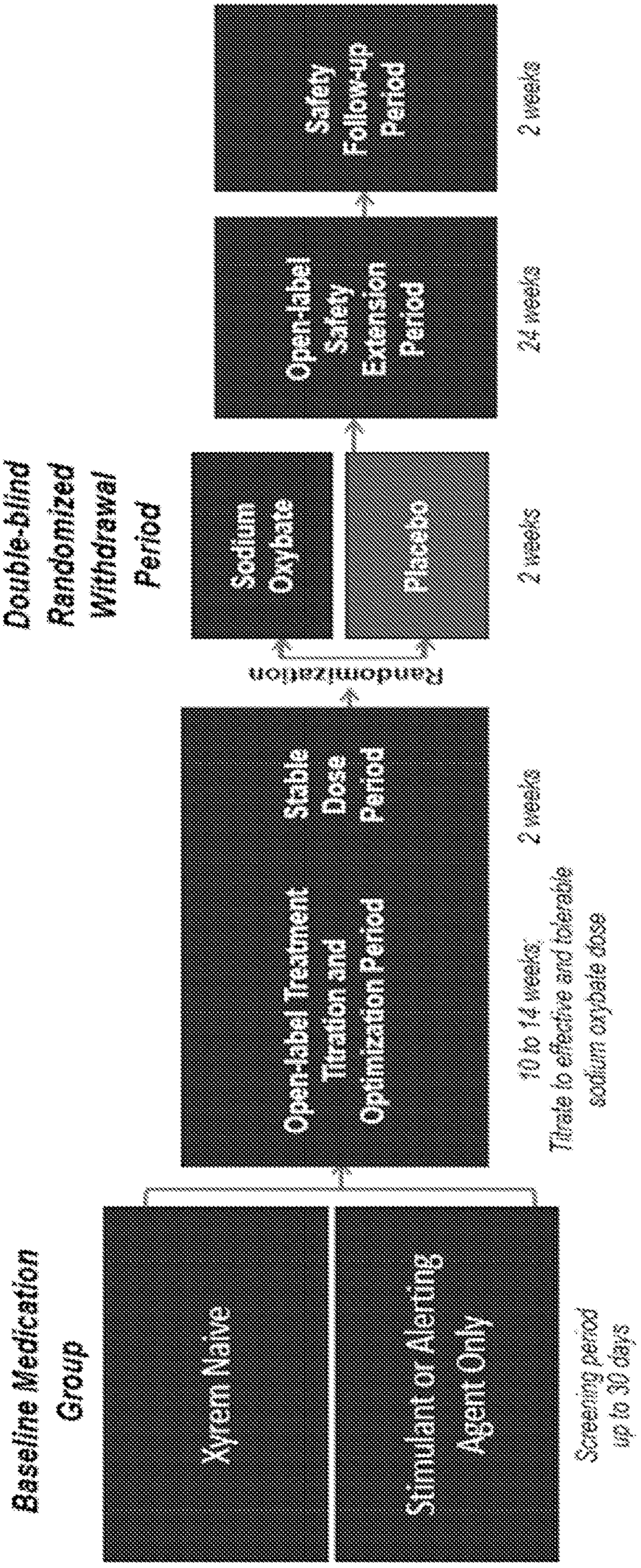
FIG. 6 shows the study design for the clinical study described in Example 2.

This is a study of the efficacy and safety of sodium oxybate (Xyrem) oral solution in subjects with Idiopathic Hypersomnia. The study design is analogous to the study described in Example 1. FIG. 6 shows the study design.

During the Open-label Treatment Titration and Optimization Period subjects will initiate sodium oxybate as either as a once or twice nightly dosing regimen at the discretion of the investigator. The dosing regimen of sodium oxybate may be adjusted as described in Example 1 until an optimally effective and tolerable dose regimen is established. The aim of the sodium oxybate dose titration and optimization is to maximize efficacy (reduction in IH symptoms, e.g., EDS, sleep inertia, and long sleep duration) while ensuring adequate nocturnal sleep and minimizing risk associated with safety and tolerability.

Subjects who have reached an optimized dosing regimen, and who have completed the Open label Treatment Titration and Optimization Period, will then enter the 2-week Stable Dose Period as described in Example 1.

Subjects who meet the randomization criteria at the end of the Stable Dose Period will be randomized to receive sodium oxybate at the stable dose and regimen or placebo at a volume and regimen equivalent to the sodium oxybate dose and regimen for 2 weeks. Randomization will be stratified by the subject's use of stimulant agent at baseline per the following baseline medication groups: 1) subjects not currently taking sodium oxybate but are taking a stimulant or alerting agent; or 2) subjects not currently taking sodium oxybate or a stimulant or alerting agent.

Subjects who complete the Double-blind Randomized Withdrawal Period will enter a 24-week Open-label Safety Extension Period as described in Example 1. A Safety Follow-up visit will occur 2 weeks after the Open-label Safety Extension Period (completion of study).

Results

With sodium oxybate treatment, patients show substantial improvements during the open-label titration period prior to randomization. During the randomized withdrawal portion of the trial, patients randomized to sodium oxybate showed clinically meaningful maintenance of efficacy for Epworth Sleepiness Scale (ESS) score, change in Patient Global Impression of Change (PGIc) scores and Idiopathic Hypersomnia Severity Scale (IHSS) endpoints. There was a significant worsening in patients administered placebo compared with sodium oxybate for ESS, PGIc, and IHSS. The overall safety profile was consistent with that previously reported for sodium oxybate (Xyrem).

The invention claimed is:

1. A method of treating idiopathic hypersomnia in a patient in need thereof, the method comprising:

administering a therapeutically effective amount of sodium oxybate to the patient.

2. A method of treating idiopathic hypersomnia in a patient in need thereof, the method comprising:

administering a therapeutically effective amount of sodium oxybate to the patient, wherein the sodium oxybate is administered as a liquid and the concentration of sodium oxybate in the liquid is about 500 mg/mL.

3. The method of claim 1, wherein the sodium oxybate is administered as a liquid, and the concentration of the sodium oxybate in the liquid is from 350 mg/ml-650 mg/ml.

4. The method of claim 1, wherein the method comprises:

(a) administering an initial daily dose of the sodium oxybate to the patient and (b) titrating the dose to provide the therapeutically effective amount of the sodium oxybate.

5. The method of claim 4, wherein the initial daily dose is from about 3 g to about 4.5 g of the sodium oxybate.

6. The method of claim 4, wherein the titration step (b) comprises administering ascending doses of the sodium oxybate.

7. The method of claim 1, wherein about 4.5 g to 9.0 g of the sodium oxybate is administered per day.

8. The method of claim 1, wherein the sodium oxybate is administered twice per day or once a day.

9. The method of claim 1, wherein about 4.5 g, about 6 g, about 7.5 g, or about 9 g of the sodium oxybate is administered per day.

10. The method of claim 1, wherein about 3 g, about 3.75 g, or about 4.5 g of the sodium oxybate is administered per day.

11. The method of claim 1, wherein the sodium oxybate is administered at bedtime.

12. The method of claim 2, wherein the method comprises:

(a) administering an initial daily dose of the sodium oxybate to the patient and (b) titrating the dose to provide a therapeutically effective amount of the sodium oxybate.

13. The method of claim 12, wherein the initial daily dose is from about 0.5 g to about 4.5 g of the sodium oxybate administered per day.

14. The method of claim 12, wherein the titration step (b) comprises administering ascending doses of the sodium oxybate.

15. The method of claim 14, wherein dose is increased by about 0.5 g to 1.5 g per week.

16. The method of 12, wherein the titration step (b) comprises administering descending doses of the sodium oxybate.

17. The method of claim 16, wherein dose is decreased by about 0.5 g to 9.0 g per week.

18. The method of claim 12, wherein the titration step (b) comprises switching a patient from a once a day dose to a twice a day dose of the sodium oxybate.

19. The method of claim 12, wherein the titration step (b) comprises switching a patient from a twice a day dose to a three times a day, or a once a day dose of the sodium oxybate.

20. The method of claim 2, wherein about 0.25 g-10.0 g of the sodium oxybate is administered per day.

21. The method of claim 4, wherein the initial daily dose is 4.5 g of sodium oxybate, and the dose is titrated to 6 g to 9 g of sodium oxybate per night.

22. The method of claim 4, wherein the sodium oxybate is in a mixed salt oxybate.

23. The method of claim 22, wherein the mixed salt oxybate comprises sodium oxybate, calcium oxybate, potassium oxybate, and magnesium oxybate.

24. The method of claim 23, wherein the mixed salt oxybate comprises about 8% sodium oxybate, about 23% potassium oxybate, about 21% magnesium oxybate, and about 48% calcium oxybate (% mol. eq.).

25. The method of claim 22, wherein the initial daily dose is 3.0 g of mixed salt oxybate, and the dose is titrated to 4.5 g to 9 g of mixed salt oxybate per night.

26. The method of claim 21, wherein the sodium oxybate is provided in a solid formulation.

27. The method of claim 21, wherein the sodium oxybate is present in a sustained release oxybate composition.

28. The method of claim 21, wherein the sodium oxybate is administered once daily.

29. The method of claim 22, wherein the mixed oxybate is administered once daily or twice daily.

* * * * *